(12) United States Patent
Streitenberger et al.

(10) Patent No.: US 9,155,708 B2
(45) Date of Patent: Oct. 13, 2015

(54) ORALLY ADMINISTRABLE IMMUNOSTIMULANT PRODUCT FOR AQUACULTURE

(75) Inventors: Sergio A. Streitenberger, Murcia (ES); Marcos Peñalver Mellado, Murcia (ES); José A. López Más, Murcia (ES); Yolanda Pedreño López, Murcia (ES); Juan P. Sola González, Murcia (ES); Pedro Martínez Ortiz, Murcia (ES); Victoriano Mulero Mendez, Murcia (ES); Francisco Roca Soler, Murcia (ES); Jorge Galindo Villegas, Murcia (ES)

(73) Assignee: PROBELTE PHARMA, S.A. (ES)

( * ) Notice: Subject to any disclaimer, the term of this patent is extended or adjusted under 35 U.S.C. 154(b) by 0 days.

(21) Appl. No.: 13/123,295

(22) PCT Filed: Oct. 10, 2008

(86) PCT No.: PCT/IB2008/002697
§ 371 (c)(1),
(2), (4) Date: May 31, 2011

(87) PCT Pub. No.: WO2010/041096
PCT Pub. Date: Apr. 15, 2010

(65) Prior Publication Data
US 2011/0225660 A1    Sep. 15, 2011

(51) Int. Cl.
| | |
|---|---|
| *A61K 38/00* | (2006.01) |
| *A61K 38/17* | (2006.01) |
| *A61K 38/19* | (2006.01) |
| *C12N 1/19* | (2006.01) |
| *C12N 15/12* | (2006.01) |
| *A61K 9/50* | (2006.01) |
| *A23K 1/00* | (2006.01) |
| *A23K 1/16* | (2006.01) |
| *A23K 1/18* | (2006.01) |

(52) U.S. Cl.
CPC .............. *A61K 9/5026* (2013.01); *A23K 1/004* (2013.01); *A23K 1/1631* (2013.01); *A23K 1/188* (2013.01); *A61K 38/1706* (2013.01); *A61K 38/191* (2013.01)

(58) Field of Classification Search
None
See application file for complete search history.

(56) References Cited

U.S. PATENT DOCUMENTS

| | | | |
|---|---|---|---|
| 5,622,657 A | 4/1997 | Takada | |
| 5,871,751 A * | 2/1999 | Christensen et al. | 424/234.1 |
| 7,026,156 B1 * | 4/2006 | Clark et al. | 435/252.3 |
| 2005/0244505 A1 | 11/2005 | Higbee | |

FOREIGN PATENT DOCUMENTS

| | | |
|---|---|---|
| ES | 2189608 A1 | 7/2003 |
| WO | 02/28371 A1 | 4/2002 |
| WO | 02/080884 A2 | 10/2002 |
| WO | 03/020040 A1 | 3/2003 |
| WO | 2004/002425 A1 | 3/2004 |
| WO | WO 2004/024125 A1 * | 3/2004 |
| WO | 2006/088473 A2 | 8/2006 |

OTHER PUBLICATIONS

Wang et al. (2005, FEBS J 272:1136-1147).*
Ordás et al. (Jan. 2007, Molecular Immunology 44:389-400).*
Immunostimulant, http://medical-dictionary.thefreedictionary.com, p. 1, accessed May 30, 2013.*
Immunostimulant, http://en.wikipedia.org, p. 1, accessed May 30, 2013.*
Immunostimulant, http://health.doctissimo.com/health-a-z/immunostimulant-drugs.html, p. 1, accessed May 30, 2013.*

* cited by examiner

*Primary Examiner* — Elizabeth C Kemmerer
(74) *Attorney, Agent, or Firm* — Hess Patent Law Firm LLC; Robert J. Hess

(57) ABSTRACT

An orally administrable immunostimulant product comprises a microencapsulated cytokine and an enteric protection polymer to protect the cytokine, the cytokine is a fish, mollusc or crustacean cytokine, preferably a recombinant cytokine such as tumor necrosis factor α (TNFα) over-expressed in a host microorganism.

18 Claims, 7 Drawing Sheets

| | |
|---|---|
| FE4: AAGGATCCGCTGAAGCGCATCAGCAGC | SEQ ID NO: 1 |
| RE5: AAGGATCCTTAAAGTGCAAACACACCAAA | SEQ ID NO: 2 |
| TNF-ECOF: AAAAGAATTCATGGGCAGCAGCCA | SEQ ID NO: 3 |
| TNF-ECOR: AAAAGAATTCTAGCAGCCGGATCC | SEQ ID NO: 4 |
| TNF-ECOPP: AAAAGAATTCAAAAATGTCTGGCAGCAGCCATCATC | SEQ ID NO: 5 |
| T7F: TAATACGACTCACTATAGGG | SEQ ID NO: 6 |
| T7R: GCTAGTTATTGCTCAGCGG | SEQ ID NO: 7 |
| TNFRO-BAMF: AAAAGGATCCGCTGAGGCAAATCAGCAGCAATGCC | SEQ ID NO: 8 |
| TNFRO-BAMR: AAAAGGATCCTCAAAGTGCAAACACACCGAAG | SEQ ID NO: 9 |
| PRO-GPD: GAGCTCAGTTTATCATTATC | SEQ ID NO: 10 |
| TER-GPD: GGTACCGGCCGCAAATTAAAG | SEQ ID NO: 11 |
| PIC5: GACTGGTTCCAATTGACAAGC | SEQ ID NO: 12 |
| PIC3: GCAAATGGCATTCTGACATCC | SEQ ID NO: 13 |

FIG. 1

```
              GGATCCGCTGAAGCGCATCAGCAGCAAAGCCAAGGCAGCCATCCAT     SEQ ID NO: 14
                L   K   R   I   S   S   K   A   K   A   A   I   H       SEQ ID NO: 15
TTAGAAGGTAGCTATGATGAAGACGAAGGTTTGAAAGACCAGGTGGAGTGGAAGAACGGT
 L   E   G   S   Y   D   E   D   E   G   L   K   D   Q   V   E   W   K   N   G
CAAGGCCAGGCGTTCGCTCAGGGTGGCTTCCGACTGGTGACAATAAGATCGTGATCCCA
 Q   G   Q   A   F   A   Q   G   G   F   R   L   V   D   N   K   I   V   I   P
CACACCGGCCTCTACTTCGTCTACAGCCAGGCGTCGTTCAGAGTCTCCTGCAGCGACGGC
 H   T   G   L   Y   F   V   Y   S   Q   A   S   F   R   V   S   C   S   D   G
GACGAGGAGGGAGCAGGGAGGCACCTCACACCTCTCAGCCACAGGATCTCGCGCTACTCA
 D   E   E   G   A   G   R   H   L   T   P   L   S   H   R   I   S   R   Y   S
GAGTCCATGGGCAGCGACGTGTCTCTGATGAGCGCGGTGAGGTCGGCGTGCCAGAACACC
 E   S   M   G   S   D   V   S   L   M   S   A   V   R   S   A   C   Q   N   T
GCTCAGGAGGACAGCTACAGCGACGGACGGGCTGGTACAACACCATCTACCTGGGCGCC
 A   Q   E   D   S   Y   S   D   G   R   G   W   Y   N   T   I   Y   L   G   A
GTGTTTCAGCTGAACAGAGGCGACAAACTGGAGACGGAAACCAACCAGTTGTCAGAGCTG
 V   F   Q   L   N   R   G   D   K   L   E   T   E   T   N   Q   L   S   E   L
GAGACGGACGAGGGCAAGACCTTCTTTGGTGTGTTTGCACTTTAAGGATCC
 E   T   D   E   G   K   T   F   F   G   V   F   A   L
```

FIG. 2

```
      SEQ. ID NO. 18
GAATTCAAAAATGTCTGGCAGCAGCCATCATCATCATCATCACAGCAGCGGCCTGGTGCCG    SEQ. ID NO. 16
          M  S  G  S  S  H  H  H  H  H  H  S  S  G  L  V  P      SEQ. ID NO. 17
CGCGGCAGCCATATGCTCGAGGATCCGCTGAAGCGCATCAGCAGCAAAGCCAAGGCAGCC
 R  G  S  H  M  L  E  D  P  L  K  R  I  S  S  K  A  K  A  A
ATCCATTTAGAAGGTAGCTATGATGAAGACGAAGGTTTGAAAGACCAGGTGGAGTGGAAG
 I  H  L  E  G  S  Y  D  E  D  E  G  L  K  D  Q  V  E  W  K
AACGGTCAAGGCCAGGCGTTCGCTCAGGGTGGCTTCCGACTGGTGGACAATAAGATCGTG
 N  G  Q  G  Q  A  F  A  Q  G  G  F  R  L  V  D  N  K  I  V
ATCCCACACACCGGCCTCTACTTCGTCTACAGCCAGGCGTCGTTCAGAGTCTCCTGCAGC
 I  P  H  T  G  L  Y  F  V  Y  S  Q  A  S  F  R  V  S  C  S
GACGGCGACGAGGAGGGAGCAGGGAGGCACCTCACACCTCTCAGCCACAGGATCTCGCGC
 D  G  D  E  E  G  A  G  R  H  L  T  P  L  S  H  R  I  S  R
TACTCAGAGTCCATGGGCAGCGACGTGTCTCTGATGAGCGCGGTGAGGTCGGCGTGCCAG
 Y  S  E  S  M  G  S  D  V  S  L  M  S  A  V  R  S  A  C  Q
AACACCGCTCAGGAGGACAGCTACAGCGACGGACGGGGCTGGTACAACACCATCTACCTG
 N  T  A  Q  E  D  S  Y  S  D  G  R  G  W  Y  N  T  I  Y  L
GGCGCCGTGTTTCAGCTGAACAGAGGCGACAAACTGGAGACGGAAACCAACCAGTTGTCA
 G  A  V  F  Q  L  N  R  G  D  K  L  E  T  E  T  N  Q  L  S
GAGCTGGAGACGGACGAGGGCAAGACCTTCTTTGGTGTGTTTGCACTTTAAGGATCCGGC
 E  L  E  T  D  E  G  K  T  F  F  G  V  F  A  L
TGCTAGAATTC
```

FIG. 3

```
       SEQ. ID NO. 21
GAATTCAAAAATGTCTGGCAGCAGCCATCATCATCATCATCACAGCAGCGGCCTGGTGCCG    SEQ. ID NO. 19
          M  S  G  S  S  H  H  H  H  H  H  S  S  G  L  V  P      SEQ. ID NO. 20
CGCGGCAGCCATATGCTCGAGGATCCGCTGAAGCGCATCAGCAGCAAAGCCAAAGCAGCC
 R  G  S  H  M  L  E  D  P  L  K  R  I  S  S  K  A  K  A  A
ATCCATTTAGAAGGTAGCTACGACGACGAGAGTTTGACTGCCAAGCTGGAGTGGAAGGAC
 I  H  L  E  G  S  Y  D  D  E  S  L  T  A  K  L  E  W  K  D
GGTCAAGGCCAAGCGTTCGCTCAGGGCGGCTTCCGACTGGCGAACAACCAGATTGTCATC
 G  Q  G  Q  A  F  A  Q  G  G  F  R  L  A  N  N  Q  I  V  I
CCACAAACCGGCCTCTACTTCGTCTACAGCCAGGCGTCGTTCAGAGTCTCCTGCGACGAT
 P  Q  T  G  L  Y  F  V  Y  S  Q  A  S  F  R  V  S  C  D  D
GGTGAAGAGGAAAGTGCGGGAAAACGCCTCACACCTCTCAGCCACAGGATCTGGAGCTAC
 G  E  E  E  S  A  G  K  R  L  T  P  L  S  H  R  I  W  S  Y
TCAGACTCCATAGGCAACAAAGCCTCTCTGATGAGCGCGGTGAGATCAGCGTGCCAAAAC
 S  D  S  I  G  N  K  A  S  L  M  S  A  V  R  S  A  C  Q  N
ACCGCTCAGGAGGACAGCTACAGAAGCGGACAGGGCTGGTACAACGCCATTTATCTAGGC
 T  A  Q  E  D  S  Y  R  S  G  Q  G  W  Y  N  A  I  Y  L  G
GCAGTGTTTCAGCTTAATAGAGGAGACAAACTGTGGACAGAAACTAACCAGCCATCACAG
 A  V  F  Q  L  N  R  G  D  K  L  W  T  E  T  N  Q  P  S  Q
CTGGAGACCGACGAGGGCAAGACTTTCTTTGGTGTGTTTGCACTTTAAGGATCCGGCTGC
 L  E  T  D  E  G  K  T  F  F  G  V  F  A  L
TAGAATTC
```

FIG. 4

```
SEQ. ID NO. 24
GAATTCAAAAATGTCTGGCAGCAGCCATCATCATCATCATCACAGCAGCGGCCTGGTGCCG         SEQ. ID NO. 22
        M   S   G   S   S   H   H   H   H   H   H   S   S   G   L   V   P       SEQ. ID NO. 23
CGCGGCAGCCATATGCTCGAGGATCCGCTGAGGCAAATCAGCAGCAATGCCAAGGCAGCC
 R   G   S   H   M   L   E   D   P   L   R   Q   I   S   S   N   A   K   A   A
ATCCATTTAGAAGGTAGCTACGACGAGGACGTGAGCTCACAGGACAAGCTGGAGTGGAAG
 I   H   L   E   G   S   Y   D   E   D   V   S   S   Q   D   K   L   E   W   K
AACGGTCAAGGCCAAGCATTCGCTCAGGGCGGCTTCCGGCTGATGGAGAACCAGATCATT
 N   G   Q   G   Q   A   F   A   Q   G   G   F   R   L   M   E   N   Q   I   I
ATCCCACAAACCGGCCTTTACTTCGTCTACAGCCAGGCGTCGTTCAGGGTCTCCTGCGAC
 I   P   Q   T   G   L   Y   F   V   Y   S   Q   A   S   F   R   V   S   C   D
GATGACAGCAAGGACGGAGCGGGAAAAACGCCTCACACCCCTCAGCCACAGGATATGGCGG
 D   D   S   K   D   G   A   G   K   R   L   T   P   L   S   H   R   I   W   R
TACTCGGACTCCTTAGGCTTCAACGCGTCTCTGATGAGCGCGGTGAGGTCGGCCTGCCAG
 Y   S   D   S   L   G   F   N   A   S   L   M   S   A   V   R   S   A   C   Q
ACGGCCGCTCAGGGGGACAGCCACAGAGATGGACAGGGCTGGTACAACACCATCTATCTG
 T   A   A   Q   G   D   S   H   R   D   G   Q   G   W   Y   N   T   I   Y   L
GGTGCAGTGTTCCAGCTGTATAAAGGAGACAAACTGTGGACGGAAACCAACATGCTGTCC
 G   A   V   F   Q   L   Y   K   G   D   K   L   W   T   E   T   N   M   L   S
GAGCTGGAGACCGAGGAGGGCAAGACCTTCTTCGGTGTGTTTGCACTTTGAGGATCCGGC
 E   L   E   T   E   E   G   K   T   F   F   G   V   F   A   L
TGCTAGAATTC
```

FIG. 5

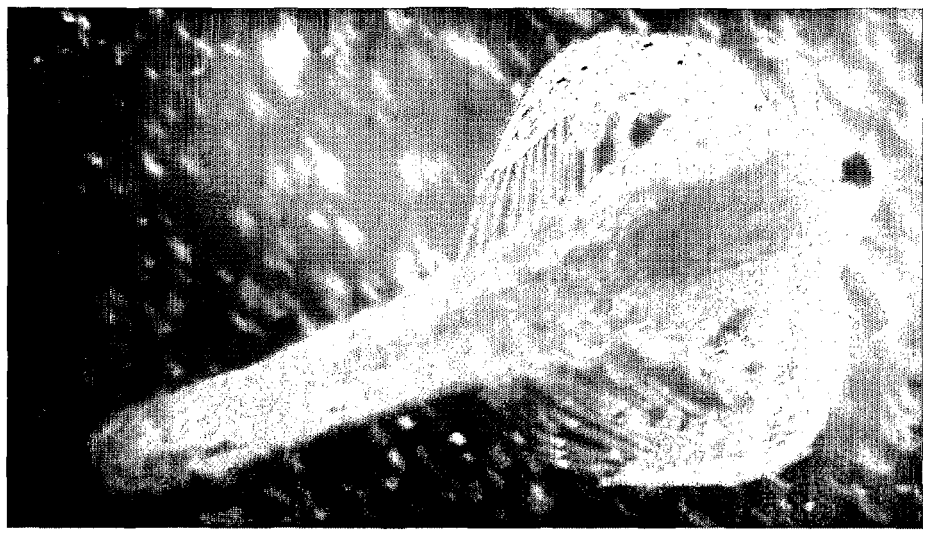
FIG. 7

ORALLY ADMINISTRABLE IMMUNOSTIMULANT PRODUCT FOR AQUACULTURE

The sequence listing entitled U.S. Ser. No. 13/123,295 Sequence Listing, created Mar. 28, 2013 and 17 KB in size, is hereby incorporated by reference.

BACKGROUND OF THE INVENTION

Aquaculture seems to be the only possibility to cover the growing demand of aquatic food that cannot be covered by extractive fishing. World aquaculture production has grown during the last fifty years from a production of less than 1 million tonnes in the early 1950s to 59.4 million tonnes by 2004. This level of production had a value of US$70.3 billion. A 69.6 percent of the world wide global production was produced in China, 21.9 in the rest of Asia and the Pacific region, 3.5 in Western European region and 0.4 in Central and Eastern European region. With regard to environment, in 2004 aquaculture production from mariculture (saltwater aquaculture) was 30.2 million tonnes, representing 50.9 percent of the global total. Freshwater aquaculture contributed 25.8 million tonnes (43.4 percent) and the remaining 3.4 million (5.7 percent) tonnes come from production in brackish environments. All the data are from *Fisheries Technical Paper* 2006, *State of World Aquaculture* (FAO).

Aquaculture production in Europe is only 3 percent of world production, but is leader in several species production, like atlantic salmon, trout, seabass, gilthead seabream, turbot and mussel. In 2002 production was higher than 1,3 million tonnes with a value of € 3280 million. The most important species in Mediterranean countries are gilthead seabream, seabass and turbot. Production of both gilthead seabream and seabass in 2002 was 181000 tonnes and principal producers were Greece, Turkey, Spain, Italy and France. Production of turbot in 2002 was 5320 tonnes from which a 75 percent was produced in Spain. All the data are from FAO.

Fish disease has become a setback to aquaculture growth and is now responsible for the severe impact on economic development in many countries of the world. Diseases cause high mortalities in many cases and it is the origin of important production losses. Aquaculture losses also cause a reduction in food availability, loss of income and employment, with all the associated social consequences. The most usual diseases and their causal agents (bacteria or virus) affecting the above mentioned species are: vibriosis (*Photobacterium damselae* subsp. *damselae, Vibrio* spp.), pasteurellosis (*Photobacterium damselae* subp. *piscicida*), photobacteriosis (*Photobacterium damselae* subsp. *pasteurella*), flexibacteriosis (*Tenacibaculum maritimum*), myxobacteriosis (*Flexibacter maritimus*), furunculosis (*Aeromonas salmonicida*), streptococcosis (*Streptococcus parauberis*), winter disease syndrome (*Pseudomonas anguilliseptica*), viral encephaloretinopathy (Nodavirus), lymphocystis (*Iridoviridae*), distended gut syndrome (virus-like particle), infective pancreatic necrosis (IPNV), infective haematopoietic necrosis (IHNV) or viral haemorrhagic septicaemia (VHS). All the data are from *Cultured Aquatic Species Information Programme* (FAO). Culture conditions of species in aquatic farmer, i.e. high densities of animals or aquatic environment, are suitable for infectious disease agents transmitted between individuals. Furthermore, the stress produced to the fish during their manipulation in the farmer could suppose a depression of immune system that facilitates infection by pathogens. Therefore, many efforts in research have been dedicated to development of vaccines or immunostimulants products to prevent diseases in fish. Prevention of diseases also reduce environmental impact because avoid massive use of antibiotics in aquaculture. Several products have been used for fish vaccination or immune system stimulation. Actually, there are vaccines available for usual bacterial fish diseases, like vibriosis, photobacteriosis, furunculosis, flexibacteriosis, winter disease syndrome or streptococcosis and also for usual viral fish diseases, like IPNV or IHNV (reviewed by Toranzo et al., 2005 and Sommerset et al., 2005).

There are three common methods of vaccination: immersion, injection and oral administration. Intraperitoneal injection is the most effective route for vaccination because it allows a better control of the dose and permits the use of adjuvant which results in better immune response. But there are disadvantages for injection route due to the fact that fish sedation and manipulation can cause a stress in animals and can origin damage to fish when vaccine is not administered with care. Moreover, small fish can not be vaccinated by this route. Immersion method is frequently used in farmer because is easy and fast but it does not allow a strict dosage control and is stressful for fish with consistent immune system depression. Oral administration of vaccines does not require fish manipulation and it is a suitable method for vaccination of all sizes animals, included juvenile fish that are starting to feed, which is very important because these fish are more susceptible to be infected by pathogens. Several disadvantages of oral route are that does not allow a strict dosage control and a large quantity of antigen is required for immunization. The most important obstacle for oral administration is that antigens are often inactivated in gut by acidic environment or protease activity and it prevent active antigens absorption by intestine. For this reason an effective oral administration requires the antigen protection, i.e: encapsulation, to avoid antigen degradation in gut (Hart et al., 1988; Quentel and Vigneulle, 1997). Different approaches to protect the antigen from degradation have demonstrated some promising results such as entrapping in liposomes or alginate microparticles (Ire et al., 2005; Maurice et al., 2004).

DESCRIPTION OF THE PRIOR ART

Immunostimulants are used in aquaculture to increase fish resistance to diseases. By chemical nature and mode of action a number of different immunostimulants have been described, such as structural elements of bacteria (LPS), various β-1,3 glucan products from bacterial and mycelial fungi, β-1,3/1,6 glucans from the cell wall of yeast, complex carbohydrate structures (glycans) from various biological sources, peptides present in extracts of certain animals or made by enzymatic hydrolysis of fish protein, nucleotides, synthetic products (levamisole) and vitamin C (reviewed by Raa, 1996). Some of the used immunostimulants also enhance specific antibody responses (reviewed by Sakai, 1999). Several states are suitable for immunostimulants use in aquaculture, such as fish manipulation, water temperature changes, higher pathogens exposition, vaccines adjuvants and all stressful situations. A number of studies have been published about effects of immunostimulants in gilthead seabream immune system, such as cell wall *Saccharomyces cerevisiae* (Ortuño et al., 2002; Rodriguez et al., 2003), chitin (Esteban et al., 2000; Esteban et al., 2001; Cuesta et al., 2003), vitamin C and E (Cuesta et al., 2002; Ortuño et al., 2003) and levamisole (Mulero et al., 1998; Cuesta et al., 2002). Among the immunostimulants known to be effective in fish, glucan, chitin and levamisole enhance phagocytic activities, while yeast glucan and vitamin C also activate complement activity.

Several studies in relation to B-1,3/1,6 glucan application as immunostimulants have been published with good results relative to increase survival rate in halibut larvae during critical phase of their development (Ottesen, Lunde and Engstad, 1999), enhance the resistance to bacterial diseases (Raa et al., 1990; Robertsen et al., 1990) and enhance the efficacy of vaccines (Raa et al., 1990; Rorstad, Aasjord and Robertsen, 1993).

Cytokines are proteins that belong to the general definition of "immunomodulators" as they regulate an amount of important biological processes, such as cell grown, cell activation, inflammation, immunity, tissue repair, fibrosis and morphogenesis. Cytokines are a diverse group of proteins that share several properties and are critical to the development and functioning of both the mediate effectors phases both innate and adaptative immune response. Last years a high number of cytokines have been cloned and sequenced in several fish species (reviewed by Bird et al., 2002). Cytokines can be classified by their function in four groups:
  a) cytokines that mediate innate immunity. The best characterized cytokines in fish of this group are type I interferon (IFN), that include IFN α and IFN β, interleukin 1 (IL-1) family that comprise IL-1 α, IL-1 β, IL-1 receptor antagonist and IL-18 and tumor necrosis factor (TNF) family include TNF α, TNF β, Ltβ and Fas ligand, being TNFα most important member with regulatory functions in immune system;
  b) cytokines that regulate haematopoiesis;
  c) cytokines that regulate lymphocytes and
  d) cytokines that control unspecific effectors cells.

The best characterized cytokine in fish in these groups are interleukin 2 (IL-2) in case of group b) and interferon gamma (IFNγ) and transforming growth factor beta (TGFβ) with respect to group c).

TNFα is an inflammatory cytokine produced by monocytes/macrophages during acute inflammation and is responsible for a diverse range of signalling events within cells. TNFα plays a role as an important mediator in resistance against parasitic, bacterial and viral infections (Czarniecki, 1993; Goldfeld and Tsai, 1996; Steinshamn et al., 1996). TNFα has also other important therapeutic functions, which include resistance to tumors (Vilcek and Lee, 1991), sleep regulation (Krueger et al., 1998) and embryonic development (Wride and Sanders, 1995). TNFα exerts many of these effects by binding, as a trimer, to a cell membrane receptor, TNFR-1 or TNFR-2 (Dembic et al., 1990; Loetscher et al., 1990), both receptors being present in great numbers on most cells (Letscher et al., 1991; Schoenfeld et al., 1991).

The TNFα mRNA seems to be transcribed in a wide variety of cells and it is largely regulated at the posttranscriptional level (Han et al., 1990). TNFα exists in two forms, a membrane-bound and a soluble form, each form possibly having a distinct physiological role (Watts et al., 1997). TNFα is expressed as a 26 kDa membrane-bound precursor, which is proteolytically cleaved by a disintegrin metalloproteinase (TACE: TNF alpha converting enzyme) to give a 17 kDa C-terminal active form (Black et al., 1997; Moss et al., 1997).

TNFα gen of several mammalian have been sequenced totally or partially, which include human (Pennica et al., 1984), chimpanzee (Kutsi et al., 2002), mouse (Shirai et al., 1988), dog (Zucker et al., 1994) or cat (McGraw et al., 1990). Also TNFα gen or a TNFα gen fragment of several fish have been sequenced, such as black seabream (Cai et al., 2003), rainbow trout (Laing et al., 2001), carp (Saeij et al., 2003) or zebra fish (Phelan et al., 2003) or gilthead seabream (Garcia-Castillo et al., 2002).

TNFα gen of gilthead seabream has four exons and three introns and a length of 1244 pb. cDNA is composed of 1359 pb that include a open reading frame (ORF) of 762 pb, a 5' untranslated region (UTR) of 142 pb and a 3' UTR of 455 pb. Deduced protein has 253 amino acids, an estimated molecular weight of 28 kDa and present high sequence homology with other fish species TNFα, specially in C-terminal extreme involved in interaction with receptors. TNFα protein contains a transmembrane region between 37 and 54 residues and a conserved sequence Thr-Leu associated with TACE proteolytic cleavage (Garcia-Castillo et al., 2002). Therefore it is possible to distinguish between a 253 amino acids membrane-bound protein (proTNFα) and a 167 amino acids soluble protein (sbTNFα).

Expression studies revealed the constitutive expression of TNFα in all the gilthead seabream tissues examined, such as liver, gill, blood, head-kidney, peritoneal exudates, brain and spleen, being macrophages one of the main source of this molecule.

U.S. Pat. No. 5,871,751 discloses a vaccine and method for treating fish susceptible to infection by *Renibacterium salmoninarum*. The vaccine comprises killed microorganism that lack intact cell-surface-associated protein p57 and may be enteric coated for oral delivery. The enteric coating comprises a polymer coating that is impervious to dissolution and/or degradation in the stomach, but is dissolved upon passing to the higher pH environments of the intestine. A preferred embodiment of the disclosed vaccine is made using spherical sugar microspheres, that are coated with a first layer comprising the killed microorganism that lack intact cell-surface-associated protein p57 and that is then coated with an enteric-coating second layer, comprising a material that is impervious to dissolution and/or degradation in the stomach of the fish.

WO 03/020040 A1 discloses an oral vaccine that consists of a multiple-cell organism that encapsulates a single-cell organism containing an antigen. This vaccine is used to feed an aquatic animal (e.g., a fish) to be vaccinated. According to WO 03/020040, the antigen, being expressed in the single-cell microorganism, is delivered to the aquatic animal via two steps of feeding i.e. the single-cell microorganism (containing the antigen) fed to the multiple-cell organism and the multiple-cell organism fed to the aquatic animal. According to WO 03/020040, it is always required the contemporaneous presence of both the single-cell microorganism and the multiple-cell organism. The antigen to be expressed depends on whether the induced immune response is against a targeted pathogen. WO 03/020040 describes *Pseudomonas* exotoxin A (PE) as the bacterial antigen, *E. coli* as single-cell microorganism, *Artemia nauplii* as multiple-cell organism. As WO 03/020040 discloses the preparation of an orally administrable vaccine, the selected antigen strictly depends on the targeted pathogen against which the vaccine must be directed.

ES 2189608 A1 discloses a process for the production of a recombinant IL-1β of *Sparus aurata* L. and its use as vaccine adjuvant and immunostimulants in commercial fish. The production of recombinant IL-1β according to ES 2189608 is carried out by cloning it into an *Escherichia coli* expression vector. The so obtained recombinant protein is purified and used as immunostimulator and vaccine adjuvant in fish industrial cultivations. Object of the present invention is to provide an immunostimulant product suitable to be orally administered that does not undergo to hydrolysis and/or degradation and that can be completely absorbed by the organism to which it is administered.

SUMMARY OF THE INVENTION

An object of the present invention is to provide an immunostimulant product that can be directly administered to the target subject.

Also an object of the present invention is to provide an immunostimulant product that can be absorbed by the organism to which it is administered in a great amount with respect to the initial administered quantity.

Another object of the present invention is to provide an immunostimulant product that is not specifically directed against a selected pathogen or a pool of selected pathogens.

Object of the invention is also to provide a process for the preparation of an orally administrable immunostimulant product and the use of an immunostimulant product for the activation of the immune response in fish aquaculture.

Thus, the present invention provides an orally administrable immunostimulant product comprising at least a microencapsulated recombinant fish cytokine, particularly tumor necrosis factor α (TNFα), a process for the preparation of an orally administrable immunostimulant product comprising a microencapsulated recombinant fish cytokine and its use for the activation of the immune response in fish aquaculture.

One aspect of the present invention is represented by the fact that the active molecule acting as immunostimulant, i.e. the cytokine and particularly tumor necrosis factor α (TNFα) is a cytokine belonging to the same fish species whose immune response is desirably to activate. This aspect is very important, as it is therefore possible to activate the immune response of a certain species just enhancing a selected set of immunostimulators that already belongs to that specie. This means that no external factors, compounds or products are in any way administered to the specie, resulting in a great advantage in the obtained result as well as in a safer approach.

As already said and according to the present invention, the active molecule acting as immunostimulant is a cytokine obtained from the fish itself, tumor necrosis factor α (TNFα). Therefore a strange substance is not introduced in the animals when the immunostimulant product is supplied and the possibility of adverse effects is avoided.

According to the invention, the gene coding for the selected cytokine is isolated from a fish tissue and cloned in an expression vector for cytokine expression in an appropriate host microorganism. Host cells are cultured in a bioreactor using a suitable medium for optimal cytokine expression and high biomass production. According to a preferred embodiment of the present invention, the host microorganism is a yeast, preferred *Pichia pastoris* and *Saccharomyces cerevisiae*, most preferred *Pichia pastoris*. The choice of the yeast as host microorganism is not casual, as yeasts are eukaryotic microorganisms able to express the selected cytokine both outside or inside the cells, depending on the selected expression vectors. This aspect allows to decide how to express the recombinant protein, giving several advantages in the fermentation process and in the purification of the so obtained products.

The recombinant protein (either obtained alone or inside the host microorganism) is then subjected to a microencapsulation process, thus obtaining a microencapsulated protein that is ready to be administered, after optional purification steps. With "microencapsulation process" it is meant any process that is suitable to provide an at least partial coating of the recombinant cytokine, said coating being suitable to protect the cytokine from enteric degradation.

In fact, in case of oral administration of immunostimulant substances an efficient method of protection is necessary in order to avoid gut degradation of the substance as well as to allow almost complete absorption by the intestine. Microencapsulation is a technological process by which very tiny droplets or particles of liquid or solid material are surrounded or coated with a continuous film of polymeric material, thus obtaining microparticles. Microencapsulation techniques are very used in several biological and chemical systems and allow to produce a huge amount of products. According to the present invention, the main techniques used for successfully obtaining microencapsulation of the interesting and selected cytokine, expecially TNFα, is atomization by spray dried. In the technique of atomization by spray dried, an active molecule is dissolved or suspended in a melt or polymer solution and becomes trapped in the dried particle. According to the present invention, most useful polymers that have been used to protect microparticles of the recombinant protein from acidic pH present in gut, have been for example selected among: cellulose acetate phthalate, hydroxypropyl cellulose phthalate, carboxymetyl cellulose, methacrylic acid copolymers, namely methacrylic acid copolymer LS such as Eudragit L-30 and Kollicoat. Others polymers that can be used are for example selected among: maltodextrin, chitosan, gelatine, starch or arabic gum.

In the present invention, TNFα has been used as an example of cytokine that is expressed in a microorganism and then mixed with polymers to protect the protein from acidic environment of gut and protease activity. The recombinant protein, i.e. TNFα, can be used as such when the host microorganism allows its over-expression outside the cells. As an advantageous alternative, when the host microorganism over-expresses the protein internally, the same microorganism is subjected to a microencapsulation process, thus obtaining a microencapsulated microorganism, able to be used as such and presenting all the advantages already explained. The result of over-expression of the protein is dried by spray dried and added to fish diet with beneficial effects to health fish. Products developed in the present invention have an enormous importance in aquaculture market to prevent fish diseases by infections, to protect fish in some stressful circumstances and as adjuvant of vaccines.

Always according to the invention, when the immunostimulant product is directed to the treatment of adult fishes, it can be administered as such, due to the advantages given by the microencapsulation process. On the contrary, when the immunostimulant product is directed to the treatment of young fishes or fish larva, it can be possible to feed a multicellular organism such as for example *Artemia Nauplii* and subsequently feed the young fishes with this multi cellular organisms, easily eaten by the young fish populations. In both cases, the microencapsulation of the immunostimulant product allows the safe maintenance of the main characteristics and activities of the product, resulting in a great advantage.

As an example, recombinant sbTNFα of gilthead seabream has been purified and its biological activity has been assayed in vivo and in vitro. Recombinant protein contains a six histidines tag in N-terminal extreme for affinity chromatography purification and anti-polyhistidine mAb detection in immunoblotting. Intraperitoneal injection resulted in: a) priming of the respiratory burst of the peritoneal exudates and head-kidney (HK) leukocytes; b) rapid recruitment of phagocytic granulocytes to the injection site, and c) induction of granulopoiesis in the HK. sbTNFα was able to induce a strong proliferation of HK cells in vitro.

Another advantage according to the present invention is represented by the fact that the host microorganism expressing TNFα cytokine can be itself act as additional source of immunostimulants substances. Some structural elements of bacteria, glucans from the cell wall of yeast, or complex carbohydrate structures (glycans) from various biological sources can be in fact used as immunostimulants.

The invention is now illustrated by way of the following examples, carried out using TNFα of several fish species of great importance in aquaculture. However, TNFα of others fish species and others cytokines can be used when practicing the invention. However, the invention can be applied to cytokines extracted or obtained by synthesis.

BRIEF DESCRIPTION OF THE DRAWINGS

The invention will now be further disclosed in greater detail with reference to the enclosed following non-limiting examples and drawings wherein:

FIG. 1. showing the primers used for gene constructs. (SEQ ID NOS: 1-13) The EcoRI and BamHI restriction sites for cloning are shown in italics.

FIG. 2. DNA fragment containing sbTNFα of gilthead seabream and deduced protein sequence (SEQ ID NOS: 14-15). The BamHI restriction sites are shown in italics.

FIG. 3. DNA fragment containing His6-sbTNFα of gilthead seabream and deduced protein sequence for expression in *Pichia pastoris* (SEQ ID NOS: 16-17). Underlined six CAT/C codons and histidines, Emphasized ATG in consensus sequence for protein expression in *Pichia pastoris*. The EcoRI and BamHI restriction sites are shown in italics.

FIG. 4. DNA fragment containing His6-sbTNFα of seabass and deduced protein sequence for expression in *Pichia pastoris* (SEQ ID NOS: 18-20). Underlined six CAT/C codons and histidines. Emphasized ATG in consensus sequence for protein expression in *Pichia pastoris*. The EcoRI and BamHI restriction sites are shown in italics.

FIG. 5: DNA fragment containing His6-hbTNFα of turbot and deduced protein sequence for expression in *Pichia pastoris* (SEQ ID NOS: 21-24). Underlined six CAT/C codons and histidines. Emphasized ATG in consensus sequence for protein expression in *Pichia pastoris*. The EcoRI and BamHI restriction sites are shown in italics.

FIG. 7. Microscopic observation of *artemia nauplii* after 60 min feeding of stained recombinant yeast. A) *artemia nauplii* and B) fluorescent stained yeast with DTAF inside of digestive tract.

DESCRIPTION OF PREFERRED EMBODIMENTS

EXAMPLE 1

Figure 6:
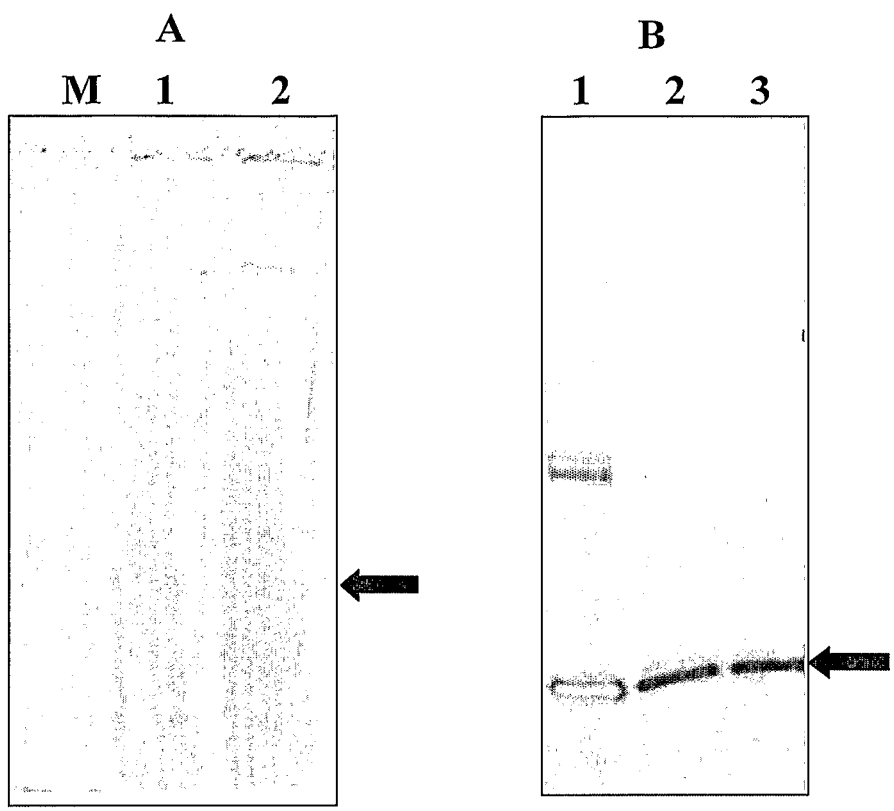
FIG. 6. showing SDS-PAGE and Western blotting with antipolyhistidine mAb (A and B respectively). Arrows indicate His6-sbTNFα of *Sparus aurata* expressed in 1) *Escherichia coli*, 2) *Saccharomyces cerevisiae* and 3) *Pichia pastoris*.

Expression of Gilthead Seabream TNFα in *Escherichia coli*

Cloning of sbTNFα into pET15b

LPS stimulated head-kidney cDNA was used as template in a PCR for amplification of sbTNFα with primers FE4 (SEQ ID NO:1) and RE5 SEQ ID NO:2) (FIG. 1). Both primers include a BamHI restriction site for posterior cloning PCR product in the same site of plasmid pET15b (Novagen). Amplification was performed in samples containing cDNA template, 50 µM of each dNTP, 0.2 mM of primers, 1× buffer PLUS containing $MgCl_2$ and 1 unit of Eco Taq PLUS DNA polymerase (Ecogen). The cycling reaction was performed in a Eppendorf Mastercycler Gradient for 1 cycle of 95° C. for 2 min, 25 cycles of 95° C. for 45 s, 60° C. for 45 s and 72° C. for 30 sec, followed by a cycle of 72° C. for 10 min. PCR product was purified with the QIAquick PCR Purification Kit (Qiagen) and ligated with plasmid pGEM-T Easy (Promega) in a relation inserfcplasmid of 3:1 using 1 unit of T4 DNA ligase (New England BioLabs, Inc.) at room temperature for 16 hours. Ligation mixture was used to transformed *Escherichia coli* DH5 µcompetent cells and spread in LB plates containing ampicillin and X-Gal (Sigma). Plates were incubated at 37° C. and several resultant white colonies were selected to test for insert presence through plasmid isolation with QIAprep Spin Miniprep Kit (Qiagen) and digestion with BamHI. A selected plasmid containing insert (sbTNFa with BamHI ends; (SEQ ID NO: 14) FIG. 2) was denominated pVP81. This plasmid and 500 ng of pET15b were digested with 10 units of BamHl for release sbTNFα of pVP81 and for pET15b linearization. Both insert and linear plasmid were purified after separation by electrophoresis in agarose low meelting (Pronadisa) gel with QIAquick Gel Extraction Kit (Qiagen) and ligated using 1 unit of T4 DNA ligase (New England BioLabs, Inc.) at room temperature for 16 hours. Ligation mixture was used to transformed *Escherichia coli* DH5α competent cells and spread in LB plates containing ampicillin. Plates were incubated at 37° C. and plasmid of several resultant colonies was isolated to test for insert release with BamHI digestion and insert orientation with PvuW digestion. A selected plasmid was sequenced with an ABI Prism 377 genetic analyzer (CIB, CSIC).

Transformation of *Escherichia coli* and Expression Assay

*Escherichia coli* BL21 (DE3) competent cells were transformed with plasmid pET15b containing sbTNFα (SEQ ID NO: 14) and mixture was spread in LB plates containing ampicillin. Several resultant colonies were cultured overnight in LB-ampicillim medium. After dilution into fresh LB-ampicillin, the cultures were grown at 37° C. to an $OD_6OO=0.8$ and induced with 1 mM isopropyl-D-thiogalactoside (IPTG; Applichem) for 0.25-4hours at either 25 or 37° C. Protein expression in whole-cell extracts was checked by centrifuging 0.1 ml of induced culture (14000 rpm) and cell pellet was lysed by boiling in SDS-loading buffer for analysis by SDS-PAGE and Western blotting using an antipolyhistidine mAb (Sigma).

EXAMPLE 2

Expression of Gilthead Seabream sbTNFα in *Saccharomyces cerevisiae*.

Cloning of $His_6$-sbTNFα into p424-GPD

Plasmid pET15b containing sbTNFα (SEQ ID NO: 14) was used as template in a PCR with TNF-ECOF (SEQ ID NO:3) and TNF-ECOR (SEQ ID NO: 4) primers (FIG. 1) for amplification of a fragment including $His_6$-sbTNFα of 613 pb. Both primers include an EcoRI restriction site for cloning PCR product in the same site of plasmid p424-GPD (ATCC 87357). Amplification was performed in samples containing 5 ng of template, 2.5 mM $MgCl_2$, 50 µM of each dNTP, 0.2 mM of primers, 1× High Speec additive, 1× buffer PLUS and 2 units of Eco Taq PLUS DNA polymerase (Ecogen). The cycling reaction was performed in a Smart Cycler II (Cepheid) for 1 cycle of 95° C. for 5 min, 30 cycles of 95° C. for 30 s, 62° C. for 45 s and 72° C. for 2 min, followed by a cycle of 72° C. for 10 min. PCR product was separated by electrophoresis in a 0.8% agarose (Pronadisa) gel containing 0.5

μg/ml ethidium bromide and purified with the QIAquick Gel Extraction Kit (Qiagen). Purified fragment and 250 ng of p424-GPD were digested with 10 units of EcoRI (Fermentas) at 37° C. previously to ligation with 5 units of T4 DNA ligase (Fermentas) at 22° C. The ligation reaction was transformed into *Escherichia coli* DH5α competent cells and colonies containing plasmid were selected in LB plates with 100 μg/ml of ampicillin. Recombinants were identified through colony PCR using 2×PCR Master Mix (Fermentas) and primers PRO-GPD and TER-GPD (FIG. 1). Resultant plasmid p424-GPD containing $His_6$-sbTNFα (SEQ ID NO: 16) was purified with QIAprep Spin Miniprep Kit (Qiagen) and tested for insert release after digestion with EcoRI and insert orientation through digestion Smap1 and Nco1. Plasmid was also sequenced with an ABI Prism 3130 genetic analyzer (SACE, University of Murcia).

Transformation of *Saccharomyces cerevisiae* and Expression Assay

*Saccharomyces cerevisiae* strain used for transformation was EGY48 (Invitrogen). To prepare EGY48 for transformation, cells of a 100 ml culture at $OD_{600}$=0.5 grown in YPD medium (2% peptone, 1% yeast extract, 2% glucose) were centrifuged at 2500 rpm for 5 min at 4° C. Following a step of waste with sterile water, cells were resuspended in 1× LiAc-TE (0.1 M lithium acetate, 10 mM Tris pH 7.5, 1 mM EDTA pH 8.0). To transformation, 10 μl of DNA at 0.3 μg/μl were mixed with 50 μl of cells and 50 μg of DNA carrier (salmon DNA previously boiled). Following it was added to mix 1× LiAc-TE-PEG (LiAc-TE as previously described and PEG 40%) and incubated at 30° C. for 30 min, prior to add DMSO to 10% and incubate at 42° C. for 10 min. Cells were spread on MMSS+SDC-Trp (minimal medium containing 2% glucose, 0.17% yeast nitrogen base, 0.25% ammonium sulphate, 1M sorbitol and SDC-Trp) plates that were incubated at 30° C. for several days until colonies appeared. SDC (synthetic dextrose complete) includes 20 mg/l adenine, arginine, histidine, tryptophane and uracil, 30 mg/l leucine, lysine, tyrosine and isoleucine, 50 mg/l phenylalanine, 200 mg/l threonine, 150 mg/l valine.

To test $His_6$-sbTNFα expression, several colonies were cultured in YPD medium or MM+SDC-Trp (minimal medium containing 2% glucose, 0.17% yeast nitrogen base, 0.25% ammonium sulphate and SDC-Trp) for several hours. To check protein expression, whole-cell extracts was disrupted by ultrasound in a Branson sonifier 150 with ten pulses of 30 sec or with glass beads in a bead beater with eight pulses of 1 min. After treatment cellular rests were harvested by centrifuging and supernatant was assayed for $His_6$-sbTNFα detection by boiling in SDS-loading buffer for analysis by SDS-PAGE and Western blotting using an antipolyhistidine mAb (Sigma).

EXAMPLE 3

Expression of Gilthead Seabream sbTNFα in *Pichia pastoris*

Cloning of $His_6$-sbTNFα into pPICZA

Plasmid pET15b containing sbTNFα (SEQ ID NO: 14) was used as template in a PCR with TNF-ECOPP (SEQ ID NO: 5) and TNF-ECOR SEQ ID NO: 4) primers (FIG. 1) for amplification of a fragment including $His_6$-sbTNFα of 618 pb. Both primers include an EcoRI restriction site for cloning PCR product in the same site of plasmid pPICZA (Invitrogen). Amplification was performed in samples containing 5 ng of template, 2.5 mM $MgCl_2$, 50 μM of each dNTP, 0.2 mM of primers, 1× High Speec additive, 1× buffer PLUS and 2 units of Eco Taq PLUS DNA polymerase (Ecogen). The cycling reaction was performed in a Smart Cycler II (Cepheid) for 1 cycle of 95° C. for 5 min, 30 cycles of 95° C. for 30 s, 55° C. for 45 s and 72° C. for 2 min, followed by a cycle of 72° C. for 10 min. PCR product was separated by electrophoresis in a 0.8% agarose (Pronadisa) gel containing 0.5 μg/ml ethidium bromide and purified with the QIAquick Gel Extraction Kit (Qiagen). Purified fragment and 200 ng of pPICZA were digested with 10 units of EcoRI (Fermentas) at 37° C., previously to ligation with 5 units of T4 DNA ligase (Fermentas) at 22° C. The ligation reaction was transformed into *Escherichia coli* TOP10F' competent cells and colonies containing plasmid were selected in LB low salt plates with 25 μg/ml of zeocin (Invitrogen). Recombinants were identified through colony PCR using 2×PCR Master Mix (Fermentas) and primers PIC5 and PIC3. The resultant plasmid pPICZA containing Hisβ-sbTNFα (SEQ ID NO: 16)was purified with QIAprep Spin Miniprep Kit (Qiagen) and tested for insert release through digestion with EcoRI and insert orientation through digestion with Xho\. Plasmid was also sequenced with an ABI Prism 3130 genetic analyzer (SACE, University of Murcia). In recombinant plasmid, star codon ATG of sbTNFα is in a yeast consensus sequence AAAAAT-GTCT (SEQ ID NO: 21 and 24) (FIG. 3), for foreign gene expression in yeast (Romanos et al., 1992). This consensus sequence was included in primer TNF-ECOPP (SEQ ID NO: 5).

Electroporation of *Pichia pastoris* and Expression Assay

Prior to electroporation of Pichia pastoris, plasmid pPICZA containing $His_6$-sbTNFα. (SEQ ID NO: 16) was linearized through digestion with Sacl or Pmel at 37° C. for latter recombination and integration in genomic DNA of *Pichia pastoris*. Total amount of 5 pg of linear plasmid were purified with the MiniElute Reaction Cleanup Kit (Qiagen) and eluted in 10 μl of sterile water. Pichia pastoris strain used for electroporation was X-33. To prepare X-33 for electroporation, cells of a 100 ml culture at $OD_6OO$ =1-5 were centrifuged at 1500× g for 5 min at 4° C. Following 2 steps of washing with sterile water, cells were resuspended in 1 M sorbitol, centrifuged as previously and resuspended finally in 1 ml of 1 M sorbitol. To electroporate, 10 μl of DNA were mixed with 80 μl of cells and transferred to an ice-cold 0.2 cm electroporation cuvette (BioRad). After incubation for 5 minutes, cells were pulsed with conditions of 25 μF, 1.5 kV and 400Ω in a MicroPulser electroporator (BioRad). Immediately it was added 1 ml of ice-cold 1 M sorbitol to the cuvette, and the resultant mix was incubated at 30° C. for 1 hour. Cells were spread on YPDS plates containing 100 μg/ml of zeocin (Invitrogen) that were incubated at 30° C. for several days until colonies appeared. Several transformants were analyzed for the presence of insert using PCR with PIC5 and PIC3 primers and 2×PCR Master Mix (Fermentas) and assayed for $HiS_6$-SbTNFa expression. In a selected colony, genomic DNA was isolated with the Genomic DNA Purification Kit (Fermentas) and DNA fragment containing $HiS_6$-SbTNFa was amplified with EcoTaq PLUS DNA polymerase (Ecogen) for sequence with an ABI Prism 3130 genetic analyzer (SACE, University of Murcia).

Recombinant *Pichia pastoris* strain with Hisβ-sbTNFα (SEQ ID NO: 16) was grown in 25 ml of minimal medium containing glycerol at 30° C. and 250 rpm to generate biomass prior to methanol induction, until culture reaches an ODβoo~6. Cells were harvested by centrifuging at 3000× g for 5 minutes and pellet was resuspended to an $OD_6OO$ ~1 in 200 ml of minimal medium containing 0.5% methanol to induce expression. Culture was incubated as previously described and 0.5% methanol was added every 24 hours to maintain induction. At several points it was recovery a sample for analyze protein expression. To check protein expression, whole-cell extracts was disrupted by ultrasound in a Branson sonifier 150 with ten pulses of 30 sec or with glass beads in a bead beater with eight pulses of 1 min. After treatment cellular rests were harvested by centrifuging and supernant was assayed for HiS$_6$-SbTNFa (SEQ ID NO: 7) detection by boiling in SDS-loading buffer for analysis by SDS-PAGE and Western blotting using an antipolyhistidine mAb (Sigma).

EXAMPLE 4

Expression of Seabass sbTNFα in *Escherichia coli*

Cloning of sbTNFα into pET15b

Seabass cDNA obtained from liver (SEQ ID NO: 19) was used as template in a PCR for amplification of sbTNFα with primers FE4 (SEQ ID NO: 1) and RE5 (SEQ ID NO:2). Both primers include a BamHI restriction site for posterior cloning PCR product in the same site of plasmid pET15b (Novagen). Amplification was performed in samples containing cDNA template, 50 μM of each dNTP, 0.2 mM of primers, 1× buffer PLUS containing MgCl$_2$ and 1 unit of Eco Taq PLUS DNA polymerase (Ecogen). The cycling reaction was performed in a Smart Cycler (Cepheid) for 1 cycle of 95° C. for 5 min, 30 cycles of 95° C. for 45 s, 55° C. for 45 s and 72° C. for 90 sec, followed by a cycle of 72° C. for 10 min. PCR product was purified with the QIAquick Gel Extraction Kit (Qiagen) after separation by electrophoresis in 0.8% agarose gel (Pronadisa). Purified fragment and plasmid pET15b were digested with 10 units of BamHI for 37° C. for 2 hours and previous DNA purification with PCR Purification Kit were ligated using 1 unit of T4 DNA ligase (Fermentas) at 22° C. o/n. Ligation mixture was used to transformed *Escherichia coli* DH5α competent cells and spread in LB plates containing ampicillin. Plates were incubated at 37° C. and recombinants were identified through colony PCR using 2×PCR Master Mix (Fermentas) and primers T7F (SEQ ID NO: 6) and T7R (SEQ ID NO: 7) (FIG. 1). Plasmid of several resultant colonies was isolated with QIAprep Spin Miniprep Kit (Qiagen) to test for insert release with BamHI digestion and insert orientation with Pvutt digestion. Recombinant plasmid was sequenced with an ABI Prism 3130 genetic analyzer (SACE, University of Murcia).

Transformation of *Escherichia coli* and Expression Assay

Transformation of *Escherichia coli* and expression assay of seabass His$_6$-sbTNFα (SEQ ID NO: 19) were performed like in EXAMPLE 1.

EXAMPLE 5

Expression of Seabass sbTNFα in *Pichia pastoris*

Cloning of His$_6$-sbTNFα into pPICZA

Cloning of His$_6$-sbTNFα of seabass (SEQ ID NO: 19) into pPICZA was performed like in EXAMPLE 3. The resultant plasmid pPICZA containing HiS$_6$-SbTNFα of seabass was sequenced with an ABI Prism 3130 genetic analyzer (SACE, University of Murcia). As in EXAMPLE 3, star codon ATG of sbTNFα is in a yeast consensus sequence AAAAATGTCT (SEQ ID NOS: 21 and 24) (FIG. 4), for foreign gene expression in yeast (Romanos et al., 1992). This consensus sequence was included in primer TNF-ECOPP (SEQ ID NO: 5)

Electroporation of *Pichia pastoris* and Expression Assay

Electroporation was performed as in EXAMPLE 3, but plasmid linearization was performed with PmeI (Fermentas). In the selected colony, DNA was isolated with the Genomic DNA Purification Kit (Fermentas) and DNA fragment containing His$_6$-sbTNFα was amplified with EcoTaq PLUS DNA polymerase (Ecogen) for sequence with an ABI Prism 3130 genetic analyzer (SACE, University of Murcia).

Expression assay was performed also as in EXAMPLE 3.

EXAMPLE 6

Expression of Turbot sbTNFα in *Escherichia coli*

Cloning of sbTNFα into pET15b

Turbot cDNA obtained from liver (SEQ ID NO: 22) was used as template in a PCR for amplification of sbTNFα with primers TNFRO-BAMF (SEQ ID NO: 8) and TNFRO-BAMR (SEQ ID NO: 9) (FIG. 1). Both primers include a BamHI restriction site for posterior cloning PCR product in the same site of plasmid pET15b (Novagen). Amplification was performed in samples containing cDNA template, 50 μM of each dNTP, 0.2 mM of primers, 1× buffer PLUS containing MgCl$_2$ and 1 unit of Eco Taq PLUS DNA polymerase (Ecogen). The cycling reaction was performed in a Smart Cycler (Cepheid) for 1 cycle of 95° C. for 5 m in, 30 cycles of 95° C. for 45 s, 55° C. for 45 s and 72° C. for 90 sec, followed by a cycle of 72° C. for 10 min. PCR product was purified with the QIAquick Gel Extraction Kit (Qiagen) after separation by electrophoresis in 0.8% agarose gel (Pronadisa). Purified fragment and plasmid pET15b were digested with 10 units of BamHI for 37° C. for 2 hours and previous DNA purification with PCR Purification Kit were ligated using 1 unit of T4 DNA ligase (Fermetas) at 22° C. o/n. Ligation mixture was used to transformed *Escherichia coli* DH5α competent cells and spread in LB plates containing ampicillin. Plates were incubated at 37° C. and recombinants were identified through colony PCR using 2×PCR Master Mix (Fermentas) and primers T7F(SEQ ID NO: 6) and T7R(SEQ ID NO: 7). Plasmid of several resultant colonies was isolated to test for insert release with BamHI digestion and insert orientation with PvuW digestion. A selected plasmid was sequenced with an ABI Prism 377 genetic analyzer (CIB, CSIC).

Transformation of *Escherichia coli* and Expression Assay

Transformation of *Escherichia coli* and expression assay of turbot His$_6$-sbTNFα were performed like in EXAMPLE 1.

EXAMPLE 7

Expression of Turbot sbTNFα in *Pichia pastoris*

Cloning of His$_6$-sbTNFα into pPICZA

Cloning of His$_6$-sbTNFα of turbot into pPICZA was performed like in EXAMPLE 3. The resultant plasmid pPICZA containing His$_6$-sbTNFα of turbot was sequenced with an ABI Prism 3130 genetic analyzer (SACE, University of Murcia). As in EXAMPLE 3, star codon ATG of sbTNFα (SEQ ID NO: 22) is in a yeast consensus sequence AAAAATGTCT (SEQ ID NOs: 18, 21 and 24) (FIGS. 3-5), for foreign gene expression in yeast (Romanos et al., 1992). This consensus sequence was included in primer TNF-ECOPP (SEQ ID NO: 5).

Electroporation of *Pichia pastoris* and Expression Assay

Electroporation was performed as in EXAMPLE 3, but plasmid linearization was performed with PmeI (Fermentas). In the selected colony, DNA was isolated with the Genomic DNA Purification Kit (Fermentas) and DNA fragment containing Hisβ-sbTNFα (SEQ ID NO: 22) was amplified with EcoTaq PLUS DNA polymerase (Ecogen) for sequence with an ABI Prism 3130 genetic analyzer (SACE, University of Murcia).ABI Prism 3130 genetic analyzer (SAGE, University of Murcia).

Expression assay was performed also as in EXAMPLE 3.

EXAMPLE 8

Purification of sbTNFα by Chromatography

His$_6$-sbTNFα expressed in E. coli, S. cerevisiae or P. pastoris was purified by affinity chromatography using an AKTA Explorer FPLC (GE Healthcare). Purification was performed with HisTrap FF columns (GE Healthcare) by immobilized metal ion affinity chromatography (IMAC) with Ni$^{2+}$, a method for purifying histidine-tagged proteins. Absorbance at 280 nm was measured by UNICORN 5.10. Column of 1 ml volume was equilibrated with at least 5 column volumes of binding buffer (20 mM sodium phosphate, 0.5 M NaCl, 5 mM imidazole, pH 7.4) with a flow rate of 1 ml/min. Then, a sample of grown culture was lysed through sonication or bead beater and further centrifuged to eliminate the pellet and obtain a clear supernatant, as in EXAMPLE 2, straight afterwards a 2 mL sample of this supernatant was loaded onto column. Column was washed with binding buffer until the absorbance reached a steady baseline (10-15 column volumes). Finally a linear gradient of 20-25 column volumes with increasing amount of elution buffer (20 mM sodium phosphate, 0.5 M NaCl, 0.5 M imidazole, pH 7.4) was applied to elute proteins bound to column. Fractions of 1 ml of eluate were collected using an automatic fraction collector. Fractions containing protein were tested for His$_6$-sbTNFα presence by SDS-PAGE and immunoblotting using an antipolyhistidine mAb (Sigma). Selected fractions were joined and amount of His$_6$-sbTNFα was assayed by Bradford (Sigma).

When it was necessary, His$_6$ tag was removed using thrombin-agarose (Recom-T; Sigma).

EXAMPLE 9

Detection of sbTNFα by SDS-PAGE and Immunoblotting

Samples with His$_6$-sbTNFα were analyzed by SDS-polyacrilamide gel electrophoresis (SDS-PAGE) with 12.5% acrilamide/bisacrilamide. Gel was stained with coomassie 0.1% for 30 min and a band of 21 kDa corresponding His$_6$-sbTNFα was distinguished.

To detect His$_6$-sbTNFα by immunoblotting, after SDS-PAGE as described above, gel was transferred to nitrocellulose membrane (Sigma) for 1 hour at 100 V in TBS (20 mM Tris-HCl, 150 mM glicine, 20% methanol. The membrane was incubated with TTBS (10 mM Tris-HCl, 100 mM NaCl, 0.1%) Tween 20) with 5% BSA to block proteins at 4° C. o/n. After washing membrane with TTBS, it was incubated with TTBS+5% BSA+1:1000 antipolyhistidine mAb (Sigma) for 2 hours. Then membrane was washed again with TTBS and TBS previously to stain with ECL (Amersham Biosciences). A single band of 21 kDa corresponding His$_6$-sbTNFα was revealed (FIG. 6).

EXAMPLE 10

Culture of Yeast by Fermentation

Cultures of transformed yeast by fermentation were carried out in a bioreactor system (Applicon).

As example, Pichia pastoris strains were cultured in a flask with YPGly medium for 24 hours until culture reaches an OD$_{600}$ higher than 30. Then the grown culture was inoculated in a Bioreactor system containing MMG (minimal medium containing glycerol). Conditions of culture were: temperature at 30° C., pH at 5.00 (controlled by addition of NH$_3$), stirred at 500-1250 rpm and oxygen at 30% in cascade with stirred. Parameters were measured by BioXpert V2. Fermenation was carried out in batch modus until cultures had reached an OD$_{600}$ of 50-80. Straight afterwards the fermentation passed to be carried out in feed-batch modus and it was started a feed with glycerol for 10 hours (cultures at OD$_{600}$ of 260-280). Finally a feed with methanol was performed for 40 hours and culture finished with an 0D$_{600}$ of 380-420.

The analysis of the expression of recombinant TNF His$_6$-sbTNFα was analyzed by immunoblotting (see example 9).

EXAMPLE 11

Microencapsulation of Recombinant Yeast

After the fermentation reached the desired biomass and optimal expression of recombinant TNF His$_6$-sbTNFα, broth was aseptically harvested and was formulated with 20% of malodextrin and 10% protected polymer Kollicoat MAE 100 P (BASF).

The formulated suspension was them pumped through a spray drier (Buchi), the inlet temperature was controlled at 120° C. and outlet temperature at 85° C.

The final microcapsules of recombinant yeast were analysed to determine the absence of cell viability and the presence of TNF His$_6$-sbTNFα by immunoblotting (see example 10).

EXAMPLE 12

Enrichment of Artemia nauplii with Microencapsulated Recombinant Yeast

Artemia nauplii were hatched (decapsulated eggs) overnight in a flask with 500 ml of sterile full-strength seawater, aerated through an air-hose connected to an aquarium airpump and maintained at 28° C. in a reciprocal-shaking water bath. Twenty four hours after hatching the nauplii were harvested to the enrichment system. This system consisted of flasks with 100 ml of clean seawater, placed in the same water bath and individually aerated. For all the experiments the percentage of hatching and the number of nauplii was estimated by taking ten samples of 0.5 ml of the seawater.

The optimal time of preparation enriched artemia nauplii with microencapsulated recombinant yeast was evaluated staining the yeast with DTAF. Then, stained yeast were used to feed artemia nauplii. The artemia nuplii were killed at time 0, 30, 45, 60 and 120 min after feeding. The enrichment artemia was observed with a fluorescence microscopy.

The results (FIG. 7) show that the amount of the microencapsulated recombinant yeast increases after feeding, first, were observed in the oral region, and later the whole intestine was full of microencapsulated recombinant yeast and no individual cells could be distinguish.

The optimal time to enrichment artemia nauplii was 60 min.

EXAMPLE 13

Expression and Secretion of Gilthead Seabream sbTNFα in Pichia pastoris

Cloning of His$_6$-sbTNFα into pPICZαA

Plasmid pET15b containing sbTNFα (SEQ ID NO: 14) was used as template in a PCR with TNF-ECOF (SEQ ID NO: 3)and TNF-ECOR (SEQ ID NO: 4) primers (FIG. 1) for amplification of a fragment including His$_6$-sbTNFα of 615 pb. Both primers include an EcoRI restriction site for cloning PCR product in the same site of plasmid pPICZαA (Invitrogen). Amplification was performed in samples containing 5 ng of template, 2.5mM $MgCl_2$, 50 µM of each dNTP, 0.2 mM of primers, 1× High Speec additive, 1× buffer PLUS and 2 units of Eco Taq PLUS DNA polymerase (Ecogen). The cycling reaction was performed in a Smart Cycler II (Cepheid) for 1 cycle of 95° C. for 5 min, 30 cycles of 95° C. for 30 s, 55° C. for 45 s and 72° C. for 2 min, followed by a cycle of 72° C. for 10 min. PCR product was separated by electrophoresis in a 0.8% agarose (Pronadisa) gel containing 0.5 µg/ml ethidium bromide and purified with the QIAquick Gel Extraction Kit (Qiagen). Purified fragment and 200 ng of pPICZA were digested with 10 units of EcoRI (Fermentas) at 37° C., previously to ligation with 5 units of T4 DNA ligase (Fermentas) at 22° C. The ligation reaction was transformed into Escherichia coli TOP10F' competent cells and colonies containing plasmid were selected in LB low salt plates with 25 µg/ml of zeocin (Invitrogen). Recombinants were identified through colony PCR using 2×PCR Master Mix (Fermentas) and primers PICα and PIC3. The resultant plasmid pPIC-ZαA containing $His_6$-sbTNFα was purified with QIAprep Spin Miniprep Kit (Qiagen) and tested for insert release through digestion with EcoRI and insert orientation through digestion with NdeI. Plasmid was also sequenced with an ABI Prism 3130 genetic analyzer (SACE, University of Murcia). Electroporation of Pichia pastoris and Expression Assay Prior to electroporation of Pichia pastoris, plasmid pPIC-ZαA containing $His_6$-sbTNFα was linearized through digestion with SacI or PmeI at 37° C. for latter recombination and integration in genomic DNA of Pichia pastoris. Total amount of 5 µg of linear plasmid were purified with the MiniElute Reaction Cleanup Kit (Qiagen) and eluted in 10 µl of sterile water. Pichia pastoris strain used for electroporation was X-33. To prepare X-33 for electroporation, cells of a 100 ml culture at $OD_{600}$=1.5 were centrifuged at 1500×g for 5 min at 4° C. Following 2 steps of washing with sterile water, cells were resuspended in 1 M sorbitol, centrifuged as previously and resuspended finally in 1 ml of 1M sorbitol. To electroporate, 10 µl of DNA were mixed with 80 µl of cells and transferred to an ice-cold 0.2 cm electroporation cuvette (BioRad). After incubation for 5 minutes, cells were pulsed with conditions of 25 µF, 1.5 kV and 400Ω in a MicroPulser electroporator (BioRad). Immediately it was added 1 ml of ice-cold 1 M sorbitol to the cuvette, and the resultant mix was incubated at 30° C. for 1 hour. Cells were spread on YPDS plates containing 100 µg/ml of zeocin (Invitrogen) that were incubated at 30° C. for several days until colonies appeared. Several transformants were analyzed for the presence of insert using PCR with PIC5 and PIC3 primers and 2× PCR Master Mix (Fermentas) and assayed for $His_6$-sbTNFα expression. In a selected colony, genomic DNA was isolated with the Genomic DNA Purification Kit (Fermentas) and DNA fragment containing $His_6$-sbTNFα was amplified with EcoTaq PLUS DNA polymerase (Ecogen) for sequence with an ABI Prism 3130 genetic analyzer (SACE, University of Murcia).

Recombinant Pichia pastoris strain with $His_6$-sbTNFα was grown in 25 ml of minimal medium containing glycerol at 30° C. and 250 rpm to generate biomass prior to methanol induction, until culture reaches an $OD_{600}$ ~6. Cells were harvested by centrifuging at 3000×g for 5 minutes and pellet was resuspended to an $OD_{600}$ ~1 in 200 ml of minimal medium containing 0.5%) methanol to induce expression. Culture was incubated as previously described and 0.5% methanol was added every 24 hours to maintain induction. At several points it was recovery a sample for analyze protein expression. To check protein expression, supernants of samples were assayed for $His_6$-sbTNFα detection by boiling in SDS-loading buffer for analysis by SDS-PAGE and Western blotting using an antipolyhistidine mAb (Sigma).

EXAMPLE 14

Efficacy of Microencapsulated Recombinant Yeast

Healthy specimens of gilthead seabream Sparus aurata L. (Sparidae, Perciform, Teleostei), with a body weight of 120 g, were kept in 2 $m^3$ running seawater aquaria (dissolved oxygen 6 ppm, flow rate 20% aquarium volume/hour) with natural temperature and photoperiod, and fed twice a day with a commercial pellet diet (Trouvit, Burgos, Spain). Experimental groups were fed with his basal diet but supplemented with 0.1, 1 or 10% control yeast or microencapulated yeast overexpressing the mature (active) sbTNFα every two days. At all sampling times (2, 4, 6 and 10 days post-treatment) the specimens were weighed and the head-kidney and intestine were removed and processed for light microscopy and gene expression studies. The experiments described comply with the Guidelines of the European Union Council (86/609/EU) and the Bioethical Committee of the University of Murcia (Spain) for the use of laboratory animals Respiratory burst activity was measured as the luminol-dependent chemiluminescence produced by head-kidney leukocyte suspensions after different stimulation times (Sepulcre et al. 2007). All experiments were performed with five fish and triplicate samples. The same experiment was repeated twice to validate the results. The SPSS 13.0.1 statistical software package was used for all statistical analysis. Data were analyzed by analysis of variance (ANOVA) and a Tukey multiple range test to determine differences between groups.

Figure 8:
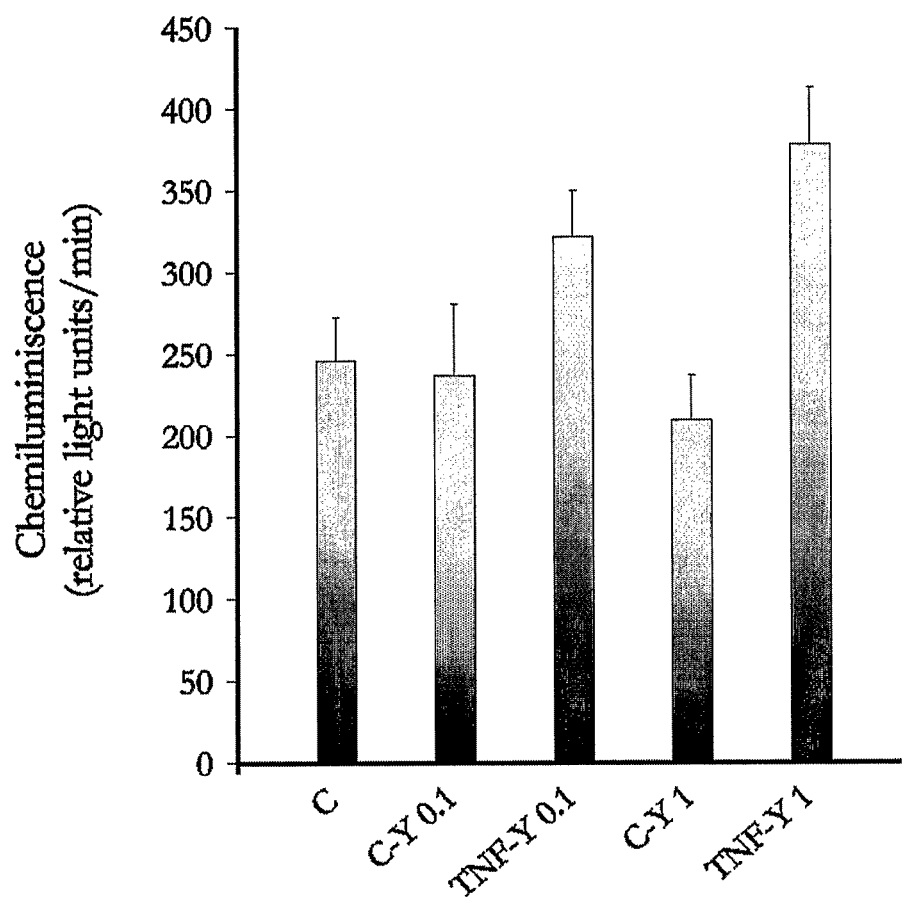
FIG. 8. Respiratory burst activity by luminol-dependent chemiluminiscense produced by head-kidney leukocytes.
Figure 9:
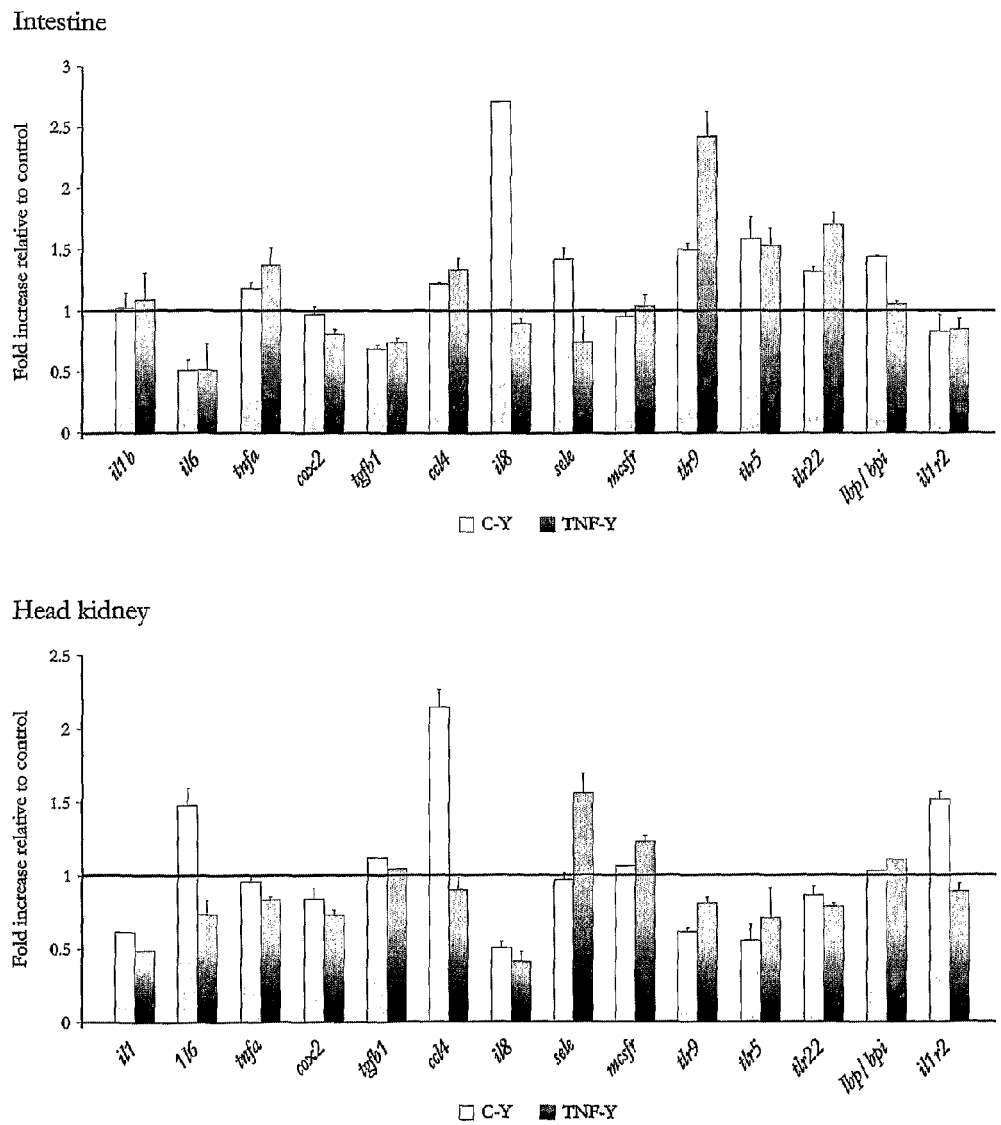
FIG. 9. mRNA levels of several inflammatory genes in the head-kidney and intestine.

The appetite, growth rate, swimming behaviour, and external morphology of fish were unaffected by the treatments and no mortality was observed during the trial. In addition, no histopathological lesions not infiltration of phagocytes (i.e. acidophilic granulocytes and macrophages) were observed in the intestine of fish fed with yeast containing sbTNFα for up to 10 days. The administration of yeast alone did not significantly affect the immunological status of the fish, assayed as the respiratory burst of head-kidney leukocytes. In sharp contrast, fish fed 0.1 and 1% of the microencapsulated yeast over-expressing the sbTNFα showed a dose-dependent increased respiratory burst 4 days post-treatment (FIG. 8). Surprisingly, the administration of yeast had no significant impact on the mRNA levels of several inflammatory genes in the head-kidney and intestine, with the exception of the TLR9, whose expression was significantly up-regulated (FIG. 9).

The above results indicate that the administration of the immunostimulant for up to 10 days has no any side effect on the fish. As the respiratory burst activity is widely used as an indication of the immunological status of the fish (Mulero et al., 1998, Garcia-Castillo et al., 2004; Chaves-Pozo et al., 2005; Sepulcre et al., 2007), the activation of this response in fish fed with yeast containing TNFα indicates that this immunostimulant is efficient and would protect the fish against abiotic (i.e stress caused by fish manipulation) and biotic (pathogens) stress. In addition, the up-regulation of the expression of TLR9 in the intestine by the administration of this immunostimulant also suggest that the intestinal tract of fish will be better protected against viral and bacterial infection, since this receptor is a key component of the recognition of these pathogens (Ishii and Akira, 2006). Collectively, all the above results also indicates that the recombinant sbTNFα will be an excellent adjuvant of oral vaccines through the systemic activation of innate immune cells and the increase of the expression of TLR9.

SEQUENCE LISTING

<160> NUMBER OF SEQ ID NOS: 24

<210> SEQ ID NO 1
<211> LENGTH: 27
<212> TYPE: DNA
<213> ORGANISM: Artificial Sequence
<220> FEATURE:
<223> OTHER INFORMATION: primer used for gene construct of the invention

<400> SEQUENCE: 1
aaggatccgc tgaagcgcat cagcagc                                27

<210> SEQ ID NO 2
<211> LENGTH: 29
<212> TYPE: DNA
<213> ORGANISM: Artificial Sequence
<220> FEATURE:
<223> OTHER INFORMATION: primer used for gene construct of the invention

<400> SEQUENCE: 2
aaggatcctt aaagtgcaaa cacaccaaa                              29

<210> SEQ ID NO 3
<211> LENGTH: 24
<212> TYPE: DNA
<213> ORGANISM: Artificial Sequence
<220> FEATURE:
<223> OTHER INFORMATION: primer used for gene construct of the invention

<400> SEQUENCE: 3
aaaagaattc atgggcagca gcca                                   24

<210> SEQ ID NO 4
<211> LENGTH: 24
<212> TYPE: DNA
<213> ORGANISM: Artificial Sequence
<220> FEATURE:
<223> OTHER INFORMATION: primer used for gene construct of the invention

<400> SEQUENCE: 4
aaaagaattc tagcagccgg atcc                                   24

<210> SEQ ID NO 5
<211> LENGTH: 36
<212> TYPE: DNA
<213> ORGANISM: Artificial Sequence
<220> FEATURE:
<223> OTHER INFORMATION: primer used for gene construct of the invention

<400> SEQUENCE: 5
aaaagaattc aaaaatgtct ggcagcagcc atcatc                      36

<210> SEQ ID NO 6
<211> LENGTH: 20
<212> TYPE: DNA
<213> ORGANISM: Artificial Sequence
<220> FEATURE:
<223> OTHER INFORMATION: primer used for gene construct of the invention

<400> SEQUENCE: 6
taatacgact cactataggg                                        20

<210> SEQ ID NO 7
<211> LENGTH: 19
<212> TYPE: DNA
<213> ORGANISM: Artificial Sequence

```
<220> FEATURE:
<223> OTHER INFORMATION: primer used for gene construct of the invention

<400> SEQUENCE: 7
gctagttatt gctcagcgg                                             19

<210> SEQ ID NO 8
<211> LENGTH: 35
<212> TYPE: DNA
<213> ORGANISM: Artificial Sequence
<220> FEATURE:
<223> OTHER INFORMATION: primer used for gene construct of the invention

<400> SEQUENCE: 8
aaaaggatcc gctgaggcaa atcagcagca atgcc                           35

<210> SEQ ID NO 9
<211> LENGTH: 32
<212> TYPE: DNA
<213> ORGANISM: Artificial Sequence
<220> FEATURE:
<223> OTHER INFORMATION: primer used for gene construct of the invention

<400> SEQUENCE: 9
aaaaggatcc tcaaagtgca aacacaccga ag                              32

<210> SEQ ID NO 10
<211> LENGTH: 20
<212> TYPE: DNA
<213> ORGANISM: Artificial Sequence
<220> FEATURE:
<223> OTHER INFORMATION: primer used for gene construct of the invention

<400> SEQUENCE: 10
gagctcagtt tatcattatc                                            20

<210> SEQ ID NO 11
<211> LENGTH: 21
<212> TYPE: DNA
<213> ORGANISM: Artificial Sequence
<220> FEATURE:
<223> OTHER INFORMATION: primer used for gene construct of the invention

<400> SEQUENCE: 11
ggtaccggcc gcaaattaaa g                                          21

<210> SEQ ID NO 12
<211> LENGTH: 21
<212> TYPE: DNA
<213> ORGANISM: Artificial Sequence
<220> FEATURE:
<223> OTHER INFORMATION: primer used for gene construct of the invention

<400> SEQUENCE: 12
gactggttcc aattgacaag c                                          21

<210> SEQ ID NO 13
<211> LENGTH: 21
<212> TYPE: DNA
<213> ORGANISM: Artificial Sequence
<220> FEATURE:
<223> OTHER INFORMATION: primer used for gene construct of the invention

<400> SEQUENCE: 13
gcaaatggca ttctgacatc c                                          21
```

<210> SEQ ID NO 14
<211> LENGTH: 517
<212> TYPE: DNA
<213> ORGANISM: Artificial Sequence
<220> FEATURE:
<223> OTHER INFORMATION: Cloning of sbTNF-alpha into pET15b (Novagen)
<220> FEATURE:
<221> NAME/KEY: misc_recomb
<222> LOCATION: (1)..(517)
<223> OTHER INFORMATION: DNA fragment containing sbTNF-alpha of
      gilthead seabream according to Example 1 and Fig 2 of the
      application as filed. DNA sequence contains BamHI restriction
      sites.

<400> SEQUENCE: 14

```
ggatccgctg aagcgcatca gcagcaaagc caaggcagcc atccatttag aaggtagcta    60
tgatgaagac gaaggtttga agaccaggt ggagtggaag aacggtcaag gccaggcgtt    120 cgctcaggt ggcttccgac tggtggacaa taagatcgtg atcccacaca ccggcctcta    180
cttcgtctac agccaggcgt cgttcagagt ctcctgcagc gacggcgacg aggagggagc    240
agggaggcac ctcacacctc tcagccacag gatctcgcgc tactcagagt ccatgggcag    300
cgacgtgtct ctgatgagcg cggtgaggtc ggcgtgccag acaccgctc aggaggacag    360 ctacagcgac ggacggggct ggtacaacac catctacctg ggcgccgtgt tcagctgaa    420 cagaggcgaa aaactggaga cggaaaccaa ccagttgtca gagctggaga cggacgaggg    480
caagaccttc tttggtgtgt ttgcacttta aggatcc                           517
```

<210> SEQ ID NO 15
<211> LENGTH: 167
<212> TYPE: PRT
<213> ORGANISM: Artificial Sequence
<220> FEATURE:
<223> OTHER INFORMATION: protein sequence of cloning sbTNF-alpha of
      gilthead seabream into pET15b

<400> SEQUENCE: 15

```
Leu Lys Arg Ile Ser Ser Lys Ala Lys Ala Ala Ile His Leu Glu Gly
1               5                   10                  15

Ser Tyr Asp Glu Asp Glu Gly Leu Lys Asp Gln Val Glu Trp Lys Asn
            20                  25                  30

Gly Gln Gly Gln Ala Phe Ala Gln Gly Gly Phe Arg Leu Val Asp Asn
        35                  40                  45

Lys Ile Val Ile Pro His Thr Gly Leu Tyr Phe Val Tyr Ser Gln Ala
    50                  55                  60

Ser Phe Arg Val Ser Cys Ser Asp Gly Asp Glu Gly Ala Gly Arg
65                  70                  75                  80

His Leu Thr Pro Leu Ser His Arg Ile Ser Arg Tyr Ser Glu Ser Met
                85                  90                  95

Gly Ser Asp Val Ser Leu Met Ser Ala Val Arg Ser Ala Cys Gln Asn
            100                 105                 110

Thr Ala Gln Glu Asp Ser Tyr Ser Asp Gly Arg Gly Trp Tyr Asn Thr
        115                 120                 125

Ile Tyr Leu Gly Ala Val Phe Gln Leu Asn Arg Gly Asp Lys Leu Glu
    130                 135                 140

Thr Glu Thr Asn Gln Leu Ser Glu Leu Glu Thr Asp Glu Gly Lys Thr
145                 150                 155                 160

Phe Phe Gly Val Phe Ala Leu
                165
```

<210> SEQ ID NO 16
<211> LENGTH: 601
<212> TYPE: DNA
<213> ORGANISM: Artificial Sequence
<220> FEATURE:
<223> OTHER INFORMATION: DNA fragment containing His6-sbTNF-alpha of
      gilthead seabream according to Ex. 3 and Fig.3.Sequence also
      contains EcoRI and and BamHI restriction sites.

<400> SEQUENCE: 16

```
gaattcaaaa atgtctggca gcagccatca tcatcatcat cacagcagcg gcctggtgcc      60
gcgcggcagc catatgctcg aggatccgct gaagcgcatc agcagcaaag ccaaggcagc     120
catccattta gaaggtagct atgatgaaga cgaaggtttg aaagaccagg tggagtggaa     180
gaacggtcaa ggccaggcgt tcgctcaggg tggcttccga ctggtggaca ataagatcgt     240
gatcccacac accggcctct acttcgtcta cagccaggcg tcgttcagag tctcctgcag     300
cgacggcgac gaggagggag caggaggca cctcacacct ctcagccaca ggatctcgcg      360
ctactcagag tccatgggca gcgacgtgtc tctgatgagc gcggtgaggt cggcgtgcca     420
gaacaccgct caggaggaca gctacagcga cggacggggc tggtacaaca ccatctacct     480
gggcgccgtg tttcagctga acagaggcga caaactggag acggaaacca accagttgtc     540
agagctggag acggacgagg gcaagacctt ctttggtgtg tttgcacttt aaggatccgg     600
c                                                                    601
```

<210> SEQ ID NO 17
<211> LENGTH: 193
<212> TYPE: PRT
<213> ORGANISM: Artificial Sequence
<220> FEATURE:
<223> OTHER INFORMATION: protein sequence of DNA fragment of
      His-6-sbTNF-alpha of gilthead seabream obtained according to
      Example 3 and Fig 3 of the application as filed.

<400> SEQUENCE: 17

```
Met Ser Gly Ser Ser His His His His His Ser Ser Gly Leu Val
1               5                   10                  15

Pro Arg Gly Ser His Met Leu Glu Asp Pro Leu Lys Arg Ile Ser Ser
            20                  25                  30

Lys Ala Lys Ala Ala Ile His Leu Glu Gly Ser Tyr Asp Glu Asp Glu
        35                  40                  45

Gly Leu Lys Asp Gln Val Glu Trp Lys Asn Gly Gln Gly Gln Ala Phe
    50                  55                  60

Ala Gln Gly Gly Phe Arg Leu Val Asp Asn Lys Ile Val Ile Pro His
65                  70                  75                  80

Thr Gly Leu Tyr Phe Val Tyr Ser Gln Ala Ser Phe Arg Val Ser Cys
                85                  90                  95

Ser Asp Gly Asp Glu Glu Gly Ala Gly Arg His Leu Thr Pro Leu Ser
            100                 105                 110

His Arg Ile Ser Arg Tyr Ser Glu Ser Met Gly Ser Asp Val Ser Leu
        115                 120                 125

Met Ser Ala Val Arg Ser Ala Cys Gln Asn Thr Ala Gln Glu Asp Ser
    130                 135                 140

Tyr Ser Asp Gly Arg Gly Trp Tyr Asn Thr Ile Tyr Leu Gly Ala Val
145                 150                 155                 160

Phe Gln Leu Asn Arg Gly Asp Lys Leu Glu Thr Glu Thr Asn Gln Leu
                165                 170                 175
```

Ser Glu Leu Glu Thr Asp Glu Gly Lys Thr Phe Phe Gly Val Phe Ala
            180                 185                 190

Leu

<210> SEQ ID NO 18
<211> LENGTH: 10
<212> TYPE: DNA
<213> ORGANISM: Artificial Sequence
<220> FEATURE:
<223> OTHER INFORMATION: Start codon ATG of sbTNF-alpha is in a yeast
      consensus sequence according to Fig. 3 and Ex.3, for foreign gene
      expression in yeast (Romanos et al., 1992). The consensus sequence
      is included in primer TNF-ECOPP.

<400> SEQUENCE: 18
aaaaatgtct                                                                10

<210> SEQ ID NO 19
<211> LENGTH: 609
<212> TYPE: DNA
<213> ORGANISM: Artificial Sequence
<220> FEATURE:
<223> OTHER INFORMATION: Cloning of Seabass cDNA sbTNF-alpha into pET15b
      according to Ex. 4.
<220> FEATURE:
<221> NAME/KEY: misc_recomb
<222> LOCATION: (1)..(609)
<223> OTHER INFORMATION: Seabass cDNA obtained from liver was used as
      template in a PCR for amplification of sbTNF-alpha with primers
      FE4 and RE5. Both primers include a BamHI restriction site for
      posterior cloning PCR product in the same site of plasmid pET15b
      (Novagen).

<400> SEQUENCE: 19
gaattcaaaa atgtctggca gcagccatca tcatcatcat cacagcagcg gcctggtgcc        60
gcgcggcagc catatgctcg aggatccgct gaagcgcatc agcagcaaag ccaaagcagc       120
catccattta gaaggtagct acgacgacga gagtttgact gccaagctgg agtggaagga       180
cggtcaaggc caagcgttcg ctcagggcgg cttccgactg gcgaacaacc agattgtcat       240
cccacaaacc ggcctctact tcgtctacag ccaggcgtcg ttcagagtct cctgcgacga       300
tggtgaagag gaaagtgcgg gaaaacgcct cacacctctc agccacagga tctggagcta       360
ctcagactcc ataggcaaca aagcctctct gatgagcgcg gtgagatcag cgtgccaaaa       420
caccgctcag gaggacagct acagaagcgg acagggctgg tacaacgcca tttatctagg       480
cgcagtgttt cagcttaata gaggagacaa actgtggaca gaaactaacc agccatcaca       540
gctggagacc gacgagggca agactttctt tggtgtgttt gcactttaag gatccggctg       600
ctagaattc                                                               609

<210> SEQ ID NO 20
<211> LENGTH: 192
<212> TYPE: PRT
<213> ORGANISM: Artificial Sequence
<220> FEATURE:
<223> OTHER INFORMATION: protein sequence of DNA fragment of sbTNF-alpha
      of seabass obtained according to Example 4 and Fig 4 of the
      application as filed.

<400> SEQUENCE: 20

Met Ser Gly Ser Ser His His His His His His Ser Ser Gly Leu Val
1               5                   10                  15

Pro Arg Gly Ser His Met Leu Glu Asp Pro Leu Lys Arg Ile Ser Ser
            20                  25                  30

```
Lys Ala Lys Ala Ala Ile His Leu Glu Gly Ser Tyr Asp Asp Ser
             35                  40                  45

Leu Thr Ala Lys Leu Glu Trp Lys Asp Gly Gln Gly Gln Ala Phe Ala
 50                  55                  60

Gln Gly Gly Phe Arg Leu Ala Asn Asn Gln Ile Val Ile Pro Gln Thr
 65                  70                  75                  80

Gly Leu Tyr Phe Val Tyr Ser Gln Ala Ser Phe Arg Val Ser Cys Asp
                 85                  90                  95

Asp Gly Glu Glu Ser Ala Gly Lys Arg Leu Thr Pro Leu Ser His
                100                 105                 110

Arg Ile Trp Ser Tyr Ser Asp Ser Ile Gly Asn Lys Ala Ser Leu Met
                115                 120                 125

Ser Ala Val Arg Ser Ala Cys Gln Asn Thr Ala Gln Glu Asp Ser Tyr
130                 135                 140

Arg Ser Gly Gln Gly Trp Tyr Asn Ala Ile Tyr Leu Gly Ala Val Phe
145                 150                 155                 160

Gln Leu Asn Arg Gly Asp Lys Leu Trp Thr Glu Thr Asn Gln Pro Ser
                165                 170                 175

Gln Leu Glu Thr Asp Glu Gly Lys Thr Phe Phe Gly Val Phe Ala Leu
                180                 185                 190

<210> SEQ ID NO 21
<211> LENGTH: 10
<212> TYPE: DNA
<213> ORGANISM: Artificial Sequence
<220> FEATURE:
<223> OTHER INFORMATION: Start codon ATG of seabass sbTNF-alpha
      according Ex. 5. Sequence is in a yeast consensus sequence
      AAAAATGTCT (Figure 4), for foreign gene expression in yeast.
      This consensus sequence was included in primer TNF-ECOPP.

<400> SEQUENCE: 21
aaaaatgtct                                                             10

<210> SEQ ID NO 22
<211> LENGTH: 612
<212> TYPE: DNA
<213> ORGANISM: Artificial Sequence
<220> FEATURE:
<223> OTHER INFORMATION: Cloning of turbot His6-sbTNF-alpha into pPICZA
      according to Ex. 7
<220> FEATURE:
<221> NAME/KEY: misc_recomb
<222> LOCATION: (1)..(612)
<223> OTHER INFORMATION: Turbot cDNA obtained from liver was used as
      template in a PCR for amplification of sbTNF-alpha with primers
      TNFRO-BAMF and TNFRO-BAMR. Both primers include a BamHI
      restriction site for posterior cloning PCR product in the same
      site of plasmid pET15b

<400> SEQUENCE: 22
gaattcaaaa atgtctggca gcagccatca tcatcatcat cacagcagcg gcctggtgcc      60
gcgcggcagc catatgctcg aggatccgct gaggcaaatc agcagcaatg ccaaggcagc     120
catccattta gaaggtagct acgacgagga cgtgagctca caggacaagc tggagtggaa     180
gaacggtcaa ggccaagcat tcgctcaggg cggcttccgg ctgatggaga accagatcat     240
tatcccacaa accggccttt acttcgtcta cagccaggcg tcgttcaggg tctcctgcga     300
cgatgacagc aaggacggag cgggaaaacg cctcacaccc ctcagccaca ggatatggcg     360
gtactcggac tccttaggct tcaacgcgtc tctgatgagc gcggtgaggt cggcctgcca     420
gacggccgct caggggggaca gccacagaga tggacagggc tggtacaaca ccatctatct     480
```

```
gggtgcagtg ttccagctgt ataaaggaga caaactgtgg acggaaacca acatgctgtc    540
cgagctggag accgaggagg gcaagacctt cttcggtgtg tttgcacttt gaggatccgg    600
ctgctagaat tc                                                       612
```

<210> SEQ ID NO 23
<211> LENGTH: 193
<212> TYPE: PRT
<213> ORGANISM: Artificial Sequence
<220> FEATURE:
<223> OTHER INFORMATION: protein sequence obtained from cloning turbot
      His6-sbTNF-alpha into pPICZA according Ex. 7

<400> SEQUENCE: 23

```
Met Ser Gly Ser Ser His His His His His His Ser Ser Gly Leu Val
1               5                   10                  15

Pro Arg Gly Ser His Met Leu Glu Asp Pro Leu Arg Gln Ile Ser Ser
            20                  25                  30

Asn Ala Lys Ala Ala Ile His Leu Glu Gly Ser Tyr Asp Glu Asp Val
        35                  40                  45

Ser Ser Gln Asp Lys Leu Glu Trp Lys Asn Gly Gln Gly Gln Ala Phe
50                  55                  60

Ala Gln Gly Gly Phe Arg Leu Met Glu Asn Gln Ile Ile Ile Pro Gln
65                  70                  75                  80

Thr Gly Leu Tyr Phe Val Tyr Ser Gln Ala Ser Phe Arg Val Ser Cys
                85                  90                  95

Asp Asp Asp Ser Lys Asp Gly Ala Gly Lys Arg Leu Thr Pro Leu Ser
            100                 105                 110

His Arg Ile Trp Arg Tyr Ser Asp Ser Leu Gly Phe Asn Ala Ser Leu
        115                 120                 125

Met Ser Ala Val Arg Ser Ala Cys Gln Thr Ala Ala Gln Gly Asp Ser
130                 135                 140

His Arg Asp Gly Gln Gly Trp Tyr Asn Thr Ile Tyr Leu Gly Ala Val
145                 150                 155                 160

Phe Gln Leu Tyr Lys Gly Asp Lys Leu Trp Thr Glu Thr Asn Met Leu
                165                 170                 175

Ser Glu Leu Glu Thr Glu Glu Gly Lys Thr Phe Phe Gly Val Phe Ala
            180                 185                 190

Leu
```

<210> SEQ ID NO 24
<211> LENGTH: 10
<212> TYPE: DNA
<213> ORGANISM: Artificial Sequence
<220> FEATURE:
<223> OTHER INFORMATION: Start codon ATG of turbot sbTNF-alpha is in a
      yeast consensus sequence according to Ex. 7 and Fig. 5, for
      foreign gene expression in yeast. This consensus sequence was
      included in primer TNF-ECOPP.

<400> SEQUENCE: 24

```
aaaaatgtct                                                          10
```

The invention claimed is:

1. An orally administrable immunostimulant product comprising at least a microencapsulated recombinant cytokine and an enteric protection polymer, wherein said recombinant cytokine is a fish cytokine or a mollusc cytokine or a crustacean cytokine.

2. The orally administrable immunostimulant product according to claim 1, characterized in that said microencapsulated recombinant cytokine is tumor necrosis factor α (TNFα).

3. The orally administrable immunostimulant product according to claim 1, characterized in that said microencap sulated recombinant cytokine is over-expressed in a host microorganism that is a yeast.

4. The orally administrable immunostimulant product according to claim 3, characterized in that said yeast is *Pichia pastoris*.

5. The orally administrable immunostimulant product according to any one of the claims 1, 2 to 4, characterized in that said microencapsulated recombinant cytokine is from a marine organism suitable for aquaculture selected from the group consisting of *Sparus aurata, Dicentrarchus labrax, Oncorhynchus mykiss, Psetta maxima, Dentex dentex, Diplodus puntazzo, Pagellus bogaraveo, Argyrosomus regius, Anguilla anguilla,* and *Octopus* sp.

6. The orally administrable immunostimulant product according to any one of claims 1, 2 to 4, characterized in that said product is suitable for being fed to a multi-cellular organism selected from the group consisting of *Artemia* sp. and phylum *Rotifera*.

7. The orally administrable immunostimulant product according to any one of claims 1, 2 to 4, characterized in that said cytokine and/or the host microorganism comprising the microencapsulated recombinant cytokine is microencapsulated with an enteric protection polymer.

8. The orally administrable immunostimulant product according to claim 1 prepared by a process comprising the steps of:
   selecting a fish, mollusc or crustacean cDNA coding for the cytokine;
   cloning the cDNA in an expression vector for cytokine expression in an appropriate host microorganism;
   culturing the host microorganism;
   obtaining the recombinant cytokine or a culture of the host microorganism comprising the recombinant cytokine;
   microencapsulating the recombinant cytokine or the host microorganism comprising the recombinant cytokine; and
   obtaining the microencapsulated recombinant cytokine or a microencapsulated host microorganism comprising the recombinant cytokine.

9. The orally administrable immunostimulant product prepared by the process according to claim 8, characterized in that said host microorganism is a yeast selected from the group consisting of *Pichia pastoris, Saccharomyces cerevisiae* and *Kluyveromyces lactis*.

10. The orally administrable immunostimulant product prepared by the process according to claim 8 or 9, characterized in that said microencapsulating step is carried out by atomization by spray drying in the presence of an enteric protection polymer selected from the group consisting of cellulose acetate phthalate, hydroxypropyl cellulose phthalate, carboxymetyl cellulose, methacrylic acid copolymers, maltodextrin, chitosan, gelatine, starch, and arabic gum.

11. A method of immunostimulating fish, molluscs, or crustaceans in aquaculture, the method comprising orally administering the orally administrable immunostimulant product according to any one of claims 1, 2 to 4 to fish, molluscs or crustaceans in aquaculture, wherein said fish, molluscs or crustaceans are selected from a group consisting of *Sparus aurata, Dicentrarchus labrax, Oncorhynchus mykiss, Psetta maxima, Dentex dentex, Diplodus puntazzo, Pagellus bogaraveo, Argyrosomus regius, Anguilla anguilla,* and *Octopus* sp.

12. The method according to claim 11, wherein said cytokine is from the same fish, mollusc or crustacean species that the immunostimulation is carried out.

13. The method according to claim 11, wherein said immunostimulation is carried out by administering the product together with food during feeding.

14. The method according to claim 12, wherein said immunostimulation is carried out by administering the product together with food during feeding.

15. A process for the preparation of an orally administrable immunostimulant product according to any one of claims 1, 2 to 4, characterized in that it comprises the following steps:
   selecting a fish, mollusc or crustacean cDNA coding for the cytokine;
   cloning the cDNA in an expression vector for cytokine expression in an appropriate host microorganism;
   culturing the host microorganism;
   obtaining the recombinant cytokine or a culture of the host microorganism comprising the recombinant cytokine;
   microencapsulating the recombinant cytokine or the host microorganism comprising the recombinant cytokine; and
   obtaining the microencapsulated recombinant cytokine or a microencapsulated host microorganism comprising the recombinant cytokine.

16. The process according to claim 15, characterized in that said host microorganism is a yeast selected among *Pichia pastoris, Saccharomyces cerevisiae* and *Kluyveromyces lactis*.

17. The process according to claim 15, characterized in that said microencapsulation step is carried out by atomization by spray drying in the presence of an enteric protection polymer selected from the group consisting of cellulose acetate phthalate, hydroxypropyl cellulose phthalate, carboxymethyl cellulose, methacrylic acid copolymers, maltodextrin, chitosan, gelatin, starch, and arabic gum.

18. The process according to claim 16, characterized in that said microencapsulation step is carried out by atomization by spray drying in the presence of an enteric protection polymer selected from the group consisting of cellulose acetate phthalate, hydroxypropyl cellulose phthalate, carboxymethyl cellulose, methacrylic acid copolymers, maltodextrin, chitosan, gelatin, starch, and arabic gum.

* * * * *